United States Patent [19]
Yanagi et al.

[11] Patent Number: 5,530,021
[45] Date of Patent: Jun. 25, 1996

[54] HYDRAZINE DERIVATIVE AND PESTICIDAL COMPOSITION COMPRISING SAID DERIVATIVE AS AN EFFECTIVE INGREDIENT

[75] Inventors: Mikio Yanagi, Okegawa; Hiroyasu Sugizaki, Tokyo; Tetsuya Toya, Yono; Yasuhito Kato, Yono; Hidetoshi Shirakura, Yono; Tetsuo Watanabe, Yono; Yoshimi Yajima, Namegawa-machi; Seiichirou Kodama, Yono; Akio Masui, Omiya; Toshiaki Yanai, Moriyama; Yoshihisa Tsukamoto, Kusatsu; Yoshihiro Sawada, Shiga-ken; Shinji Yokoi, Otsu, all of Japan

[73] Assignees: Nippon Kayaku Kabushiki Kaisha, Tokyo, Japan; Sankyo Company, Limited, Tokyo, Japan

[21] Appl. No.: 308,643

[22] Filed: Sep. 19, 1994

Related U.S. Application Data

[62] Division of Ser. No. 152,877, Nov. 15, 1993, Pat. No. 5,378,726, which is a continuation of Ser. No. 821,016, Jan. 15, 1992, abandoned.

[30] Foreign Application Priority Data

Jan. 25, 1991 [JP] Japan ................................ 3-23680
Oct. 17, 1991 [JP] Japan ................................ 3-298313

[51] Int. Cl.$^6$ ........................ A01N 43/32; A01N 43/24; C07D 319/20; C07D 321/10
[52] U.S. Cl. ..................... 514/452; 514/450; 549/362; 549/350
[58] Field of Search ................... 549/362, 350; 514/452, 450

[56] References Cited

U.S. PATENT DOCUMENTS

| | | | |
|---|---|---|---|
| 4,857,550 | 8/1989 | Kameswaran et al. | 514/522 |
| 4,985,461 | 1/1991 | Hsu et al. | 514/615 |
| 5,117,057 | 6/1992 | Hsu et al. | 564/149 |

FOREIGN PATENT DOCUMENTS

| | | |
|---|---|---|
| 76287/87 | 10/1988 | Australia . |
| 228564 | 7/1987 | European Pat. Off. . |
| 232075 | 8/1987 | European Pat. Off. . |
| 234944 | 9/1987 | European Pat. Off. . |
| 245950 | 11/1987 | European Pat. Off. . |
| 253468 | 1/1988 | European Pat. Off. . |
| 261755 | 3/1988 | European Pat. Off. . |
| 286746 | 10/1988 | European Pat. Off. . |
| 347216 | 12/1989 | European Pat. Off. . |
| 361645 | 4/1990 | European Pat. Off. . |
| 395581 | 10/1990 | European Pat. Off. . |
| 398842 | 11/1990 | European Pat. Off. . |
| 1275554 | 11/1989 | Japan . |
| 2207066 | 8/1990 | Japan . |
| 3141245 | 6/1991 | Japan . |
| 4894711 | 3/1992 | Japan . |
| 4178380 | 6/1992 | Japan . |
| 4235177 | 8/1992 | Japan . |
| 539252 | 2/1993 | Japan . |

*Primary Examiner*—Nicky Chan
*Attorney, Agent, or Firm*—Nields & Lemack

[57] ABSTRACT

A novel hydrazine derivative and a pesticidal composition containing the hydrazine derivative as the effecting ingredient. The hydrazine derivative show high pesticidal activity against harmful pests which are resistant to known pesticides such as organophosphorus pesticides, pyrethroids, etc., especially against Lepidoptera harmful pests such as *Plutella xylostella*, *Spodoptera litura*, *Cnaphalocrocis medinalis*, *Adoxophyes orana*, etc., and is effective for controlling harmful pests in paddy field, upland field, orchard, forest or places to be kept environmentally hygienic.

18 Claims, No Drawings

HYDRAZINE DERIVATIVE AND PESTICIDAL COMPOSITION COMPRISING SAID DERIVATIVE AS AN EFFECTIVE INGREDIENT

This application is a divisional of application Ser. No. 08/152,877 filed Nov. 15, 1993 now U.S. Pat. No. 5,378,726, which is a continuation of application Ser. No. 07/821,016 filed Jan. 15, 1992 (abandoned).

BACKGROUND OF THE INVENTION

The present invention relates to a novel hydrazine derivative which can be utilized as a pesticide in paddy field, upland field, orchard, forest or places to be kept environmentally hygiene. Also, the derivative can be utilized as a parasiticide for protecting human being or animals from injury of a parasite.

In Japanese Patent Application Laid-Open (KOKAI) No. 62-167747 (1987) (U.S. Pat. No. 4,985,461, EP 236618), No. 62-263150(1987) and No. 3-141245 (1991), there are described that N-substituted-N'-substituted-N,N'-diacylhydrazine derivative has pesticidal activity. However, in these patent publications, the derivative of the present invention mentioned below has never been described.

For controlling harmful pest in paddy field, upland field, orchard, forest or places to be kept environmentally hygiene, there have been demanded a compound having a higher pesticidal activity without damaging useful insects, circumstance, etc. and having a low toxicity to human and animal. Also, in recent years, the number of harmful pest which shows resistance to known pesticides such as an organophosphorus compound, a carbamate compound, a pyrethroid, etc. is increasing and control thereof becomes difficult whereby a new type pesticidal compound is now demanded.

SUMMARY OF THE INVENTION

The present invention is to provide a new type pesticidal compound which substantially does not affect to useful insects, environment, etc., has a low toxicity to human and animal and shows an excellent control effect against chemical-resistant harmful pests, and a pesticidal composition containing the compound as an effective ingredient.

The present inventors have investigated intensively in order to solve the above problem, and as the results, have found that a novel hydrazine derivative having an excellent pesticidal activity. The present invention has been accomplished based on this finding.

DETAILED DESCRIPTION OF THE INVENTION

The pesticidal compound of the present invention is represented by the following formula (I):

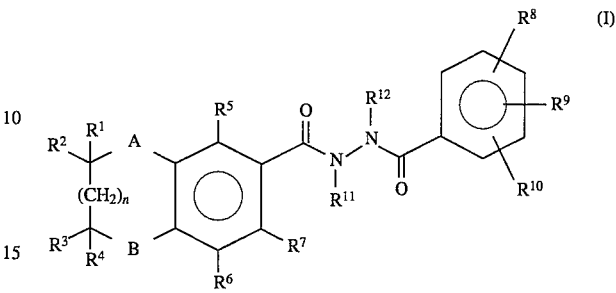

wherein
A and B each independently represent —O—, —S—,

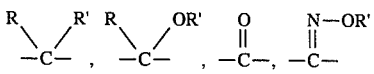

or NR' wherein R represents a hydrogen atom, $(C_1-C_4)$alkyl group or $(C_1-C_4)$alkoxy group, R' represents a hydrogen atom, $(C_1-C_4)$alkyl group, $(C_2-C_4)$acyl group or p-fluorobenzyl group, or R and R' may be combined to form an dioxolan ring together with the carbon atom to which R and R' are attached, A, B or both A and B optionally forming a double bond with an adjacent carbon atom when A and B each independently represent

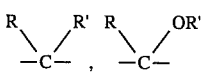

or NR';

$R^1$, $R^2$, $R^3$ and $R^4$ each independently represent hydrogen atom, halogen atom, $(C_1-C_4)$alkyl group, $(C_1-C_4)$alkoxy$(C_1-C_4)$alkyl group or benzyloxy $(C_1-C_4)$alkyl group;

$R^5$, $R^6$ and $R^7$ each independently represent hydrogen atom, halogen atom, $(C_1-C_4)$alkyl group, nitro group, amino group, cyano group, hydroxyl group, formyl group, $(C_1-C_4)$haloalkyl group, $(C_2-C_4)$alkenyl group, $(C_1-C_4)$alkoxy group, $(C_1-C_4)$alkoxy$(C_1-C_4)$alkyl group, $(C_1-C_4)$alkylthio$(C_1-C_4)$alkyl group or $(C_1-C_4)$alkoxy$(C_1-C_4)$alkoxy group, $R^8$, $R^9$ and $R^{10}$ each independently represent hydrogen atom, halogen atom, $(C_1-C_4)$alkyl group, tri$(C_1-C_4)$alkylsilyloxy$(C_1-C_4)$alkyl group, nitro group, $(C_1-C_4)$haloalkyl group, hydroxy $(C_1-C_4)$alkyl group, formyl group, $(C_1-C_4)$alkoxy group, $(C_2-C_4)$alkenyloxy group, $(C_2-C_4)$alkynyloxy group, $(C_2-C_4)$alkenyl group, $(C_2-C_4)$alkynyl group, $(C_1-C_4)$haloalkoxy group, $(C_1-C_4)$haloalkylthio group, $(C_1-C_4)$alkoxy$(C_1-C_4)$alkoxy group, $(C_1-C_4)$alkoxy group having a phenyl group which is optionally substituted by a halogen atom, or $(C_1-C_4)$alkoxy group having a phenoxy group which is optionally substituted on the phenyl group by a $CF_3$, halogen atom or $(C_1-C_2)$alkyl group;

$R^{11}$ represents a hydrogen atom, cyano group, $(C_1-C_4)$haloalkylthio group, $(C_2-C_5)$acyl group, di$(C_1-C_4)$alkylcarbamoyl group, $(C_1-C_4)$alkoxycarbonyl group, $(C_1-C_4)$alkoxycarbonylcarbonyl group, $(C_2-C_4)$alkenyl group or $(C_1-C_4)$alkyl group which is optionally substituted by a halogen atom, $(C_1-C_4)$alkoxy group, $(C_1-C_6)$alkylcarbonyloxy group or $(C_1-C_4)$alkoxycarbonyl group;

$R^{12}$ represents a branched $(C_3-C_{10})$alkyl group; and n represents 0 or 1;

with the proviso that when A and B each independently represent —O— or

wherein R and R' each independently represent a hydrogen atom or $(C_1-C_4)$alkyl group, at least one of $R^5$, $R^6$ and $R^7$ is not a hydrogen atom.

In the formula (I), the halogen atom may include fluorine atom, chlorine atom, bromine atom and iodine atom;

the $(C_1-C_4)$alkyl group may include methyl, ethyl, n-propyl, isopropyl, n-butyl, isobutyl, sec-butyl and t-butyl group;

the $(C_2-C_4)$alkenyl group may include allyl, 2-propenyl, 1-propenyl, ethenyl and 2-butenyl group;

the $(C_1-C_4)$alkoxy group may include methoxy, ethoxy, n-propoxy, isopropoxy, n-butoxy, sec-butoxy isobutoxy and t-butoxy group;

the hydroxy $(C_1-C_4)$alkyl group may include 2-hydroxyethyl and hydroxymethyl group;

the $(C_1-C_4)$alkoxy$(C_1-C_4)$alkoxy group may include ethoxymethoxy, methoxyethoxy, ethoxyethoxy, n-propoxymethoxy, isopropoxymethoxy and n-butoxymethoxy group;

the $(C_2-C_4)$alkynyl group may include ethynyl, propynyl and butynyl group;

the $(C_1-C_4)$haloalkyl group may include 1- or 2-chloroethyl, chloromethyl, dichloromethyl, bromomethyl, 1- or 2-bromoethyl, fluoromethyl, difluoromethyl and trifluoromethyl group;

the $(C_1-C_4)$haloalkoxy group may include 1- or 2-bromoethoxy, 3-bromo-n-propoxy, 2,2,2- or 1,1,2-trifluoroethoxy and trifluoromethoxy group;

the $(C_2-C_4)$alkenyloxy group may include allyloxy and 2-butenyloxy group;

the $(C_2-C_4)$alkynyloxy group may include propargyloxy and butynyloxy group;

the $(C_1-C_4)$alkoxy group having a phenyl group which is optional substituted by a halogen atom may include 2-(p-chlorophenyl)ethoxy, m-chlorophenylmethoxy, 2-(p-fluorophenyl)ethoxy, 2-(m-fluorophenyl)ethoxy and 3-(p-bromophenyl)propoxy group;

the $(C_1-C_4)$alkylthio$(C_1-C_4)$alkyl group may include methylthiomethyl, 2-methylthioethyl, 3-isopropylthiopropyl, n-butylthiomethyl and 2-ethylthioethyl group;

the tri $((C_1-C_4)$alkylsilyloxy$(C_1-C_4)$alkyl group may include trimethylsilyloxymethyl, trimethylsilyloxyethyl and dimethyl-t-butylsilyloxymethyl group;

the $(C_1-C_4)$alkoxy group having a phenoxy group which is optionally substituted by a $CF_3$, halogen atom or $(C_1-C_2)$alkyl group may include 2-(m-trifluoromethylphenoxy)ethoxy, 3-phenoxypropoxy, 2-(m-methylphenoxy)ethoxy, 2-(p-chlorophenoxy)ethoxy and 2-(p-fluorophenoxy)ethoxy group;

the $(C_1-C_4)$haloalkylthio group may include 2-chloroethylthio, 2-bromoethylthio, trichloromethylthio, fluorodichloromethylthio, trifluoromethylthio and 2-fluoropropylthio group;

the $(C_2-C_5)$acyl group may include acetyl and propionyl group;

the $(C_1-C_4)$alkoxycarbonylcarbonyl group may include t-butoxycarbonylcarbonyl, methoxycarbonylcarbonyl and ethoxycarbonylcarbonyl group;

the $(C_1-C_4)$alkoxycarbonyl group may include ethoxycarbonyl, methoxycarbonyl, isopropoxycarbonyl and isobutoxycarbonyl group;

the $(C_1-C_4)$alkyl group which is optionally substituted by a $(C_1-C_6)$alkylcarbonyloxy group or $(C_1-C_4)$alkoxycarbonyl group may include ethylcarbonyloxymethyl, 2-isopropylcarbonyloxyethyl, t-butylcarbonyloxymethyl, 2-methoxycarbonylethyl and t-butoxycarbonylmethyl group;

the $(C_1-C_4)$alkoxy$(C_1-C_4)$alkyl group may include ethoxymethyl, 3-methoxypropyl, 2-ethoxyethyl and methoxymethyl group;

the di$(C_1-C_4)$alkylcarbamoyl group may include dimethylcarbamoyl and diethylcarbamoyl group; and the branched $(C_3-C_{10})$alkyl group may include t-butyl, 1,2,2-trimethylpropyl, 2,2-dimethylpropyl and 1,2,2-trimethylbutyl group.

A preferred is a hydrazine derivative represented by the formula (I), wherein

A represents —O— or —$CH_2$—;

B represents —O— or —$CH_2$—;

$R^1$, $R^2$, $R^3$ and $R^4$ each independently represent a hydrogen atom or a methyl group;

$R^5$ represents a $(C_1-C_4)$alkyl group, a $(C_1-C_4)$haloalkyl group or a halogen atom;

$R^6$ represents a hydrogen atom, a $(C_1-C_4)$alkyl group or a halogen atom;

$R^7$ represents a hydrogen atom or a halogen atom;

$R^8$, $R^9$ and $R^{10}$ each independently represent a hydrogen atom, a $(C_1-C_4)$alkyl group, a $(C_1-C_4)$haloalkyl group, a halogen atom, a nitro group, a $(C_1-C_4)$alkoxy group, a $(C_2-C_4)$alkenyloxy group, a $(C_2-C_4)$alkynyloxy group, a $(C_2-C_4)$alkenyl group, a $(C_1-C_4)$haloalkoxy group, a phenyl $(C_1-C_4)$alkoxy group whose phenyl moiety is optionally substituted with a halogen atom, or a phenoxy $(C_1-C_4)$alkoxy group whose phenyl moiety is optionally substituted with a $(C_1-C_2)$alkyl group, $CF_3$ or halogen atom;

$R^{11}$ represents a hydrogen atom, a cyano group, a $(C_1-C_4)$haloalkylthio group, a $(C_1-C_4)$alkoxycarbonylcarbonyl group or a $(C_1-C_4)$alkylcarbonyloxymethyl group;

$R^{12}$ represents a branched $(C_4-C_8)$alkyl group; and n represents 0.

A more preferred is a hydrazine derivative represented by the formula (I) wherein A represents —O— or —$CH_2$—;

B represents —O—;

$R^1$ $R^2$ $R^3$ and $R^4$ each represent a hydrogen atom;

$R^5$ represents a $(C_1-C_2)$alkyl group, a $(C_1-C_2)$haloalkyl group or a halogen atom;

$R^6$ represents a hydrogen atom;

$R^7$ represents a hydrogen atom;

$R^8$, $R^9$ and $R^{10}$ each independently represent a hydrogen atom, a $(C_1-C_2)$alkyl group, a $(C_1-C_2)$haloalkyl group, a halogen atom, a nitro group or a $(C_1-C_2)$alkoxy group;

$R^{11}$ represents a hydrogen atom, a cyano group, a trichloromethylthio group, an ethoxycarbonyl carbonyl group or a pivaloyloxymethyl group;

$R^{12}$ represents a branched $(C_4-C_6)$alkyl group; and
n represents 0.

A further preferred is a hydrazine derivative represented by the formula (I) wherein A represents —O— or —$CH_2$—;
B represents —O—;
$R^1$, $R^2$, $R^3$ and $R^4$ each represents a hydrogen atom;
$R^5$ represents a $(C_1-C_2)$alkyl group;
$R^6$ represents a hydrogen atom;
$R^7$ represents a hydrogen atom;
$R^8$, $R^9$ and $R^{10}$ each independently represents a hydrogen atom, a methyl group, a mono-, di- or trifluoromethyl group, a chlorine atom, a fluorine atom, a nitro group or a methoxy group;
$R^{11}$ represents a hydrogen atom, a cyano group, a trichloromethylthio group, an ethoxycarbonylcarbonyl group or a pivaloyloxymethyl group;
$R^{12}$ represents a branched $(C_4-C_6)$alkyl group; and
n represents 0.

A most preferred is a hydrazine derivative represented by the formula (I) wherein A represents —O— or —$CH_2$—;
B represents —O—;
$R^1$ $R^2$ $R^3$ and $R^4$ each represents a hydrogen atom;
$R^5$ represents a $(C_1-C_2)$alkyl group;
$R^6$ represents a hydrogen atom;
$R^7$ represents a hydrogen atom;
$R^8$, $R^9$ and $R^{10}$, together with the phenyl group to which they are attached, represent a 3,5-dimethylphenyl group, a 3,5-dichlorophenyl group, a 2,4-dichlorophenyl group, a 3-fluoromethyl-5-methylphenyl group, a 3-difluoromethyl-5-methylphenyl group or a 3,5-dimethyl-4-fluorophenyl group;
$R^{11}$ represents a hydrogen atom, a cyano group or a trichloromethylthio group;
$R^{12}$ represents a t-butyl group, a 2,2-dimethylpropyl group or a 1,2,2-trimethylpropyl group; and
n represents 0.

The specifically preferred hydrazine derivatives are
N-(5-methylchroman-6-carbo)-N'-t-butyl-N'-(3,5-dimethylbenzoyl)hydrazine,
N-cyano-N-(5-methylchroman-6-carbo)-N'-t-butyl-N'-( 3,5-dimethylbenzoyl )hydrazine,
N-(5-methylchroman-6-carbo)-N'-t-butyl-N'-(3,5-dimethyl-4-fluorobenzoyl )hydrazine,
N-(5-methylchroman-6-carbo)-N-trichloromethylthio-N'-t-butyl-N'-( 3,5-dimethylbenzoyl)hydrazine,
N-(5-methyl-1,4-benzodioxan-6-carbo)-N'-(2,2dimethylpropyl)-N'-( 3,5-dimethylbenzoyl)hydrazine,
N-cyano-N-(5-methyl-1,4-benzodioxan-6-carbo)-N'-t-butyl-N'-( 3,5-dimethylbenzoyl)hydrazine,
N-(5-methyl-1,4-benzodioxan-6-carbo)-N-trichloromethylthio-N' -t-butyl-N'-(3,5-dimethylbenzoyl)hydrazine,
N-(5-methyl-1,4-benzodioxan-6-carbo)-N'-t-butyl-N'-(3,5-dichlorobenzoyl)hydrazine,
N-(5-methyl-1,4-benzodioxan-6-carbo)-N'-t-butyl-N'-(3-difluoromethyl- 5-methylbenzoyl )hydrazine,
N-(5-methyl-1,4-benzodioxan-6-carbonyl)-N'-(1,2,2-trimethylpropyl)-N'-( 3,5dimethylbenzoyl)hydrazine, and
N-(5-methyl-1,4-benzodioxan-6-carbonyl)-N'-t-butyl-N'-(3, 5-dimethylbenzoyl)hydrazine.

The hydrazine derivative of the formula (I) according to the present invention can be prepared by the method as mentioned below.

A hydrazide represented by the formula (II):

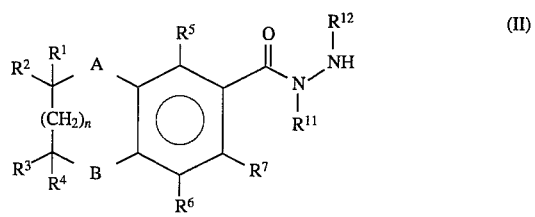

wherein
A, B, $R^1$, $R^2$, $R^3$, $R^4$, $R^5$, $R^6$, $R^7$, $R^{11}$, $R^{12}$ and n have the same meanings as defined above, and a benzoyl halide represented by the formula (III):

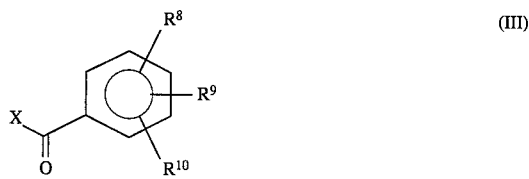

wherein
$R^8$, $R^9$ and $R^{10}$ have the same meanings as defined above, and X represents a halogen atom, are reacted in a solvent in the presence of a base to obtain the hydrazine derivative of the formula (I).

The hydrazide of the formula (II) and the benzoyl halide of the formula (III) may be reacted in an optional ratio, but preferably in an equimolar ratio or substantially equimolar ratio. As the solvent, any solvent inert to each of the reactants may be used. There may be mentioned aliphatic hydrocarbons such as hexane, heptane, etc., aromatic hydrocarbons such as benzene, toluene, xylene, etc., halogenated hydrocarbons such as chloroform, dichloromethane, chlorobenzene, etc., ethers such as diethyl ether, tetrahydrofuran, etc., nitriles such as acetonitrile, propionitrile, etc. A mixed solvent of the above or a mixed solvent of the above and water may be used. As the base, there may by used inorganic bases such as potassium hydroxide, sodium hydroxide, etc., and organic bases such as triethylamine, pyridine, etc. When organic bases such as triethylamine, pyridine, etc. are used, they may be used in large excess for use as a solvent. The base may be used in a stoichiometrical amount or in excess amount with respect to the amount of hydrogen halide to be produced during the reaction, but preferably a stoichiometrical amount or 1.0 to 5.0 time the stoichiometrical amount. The reaction can be carried out in a temperature from −20° C. to the boiling point of a solvent, but preferably in the range from −5° to 50° C. A catalyst such as N,N'-dimethylaminopyridine may be added to the reaction system.

A hydrazine derivative of the formula (I) wherein $R^{11}$ is a cyano group, $(C_1-C_4)$haloalkylthio group, $(C_2-C_5)$acyl group, di$(C_1-C_4)$alkylcarbamoyl group, $(C_1-C_4)$alkoxycarbonyl group, $(C_1-C_4)$alkoxycarbonylcarbonyl group, $(C_1-C_4)$alkyl group which is optionally substituted by a halogen atom, $(C_1-C_4)$alkoxy group, $(C_1-C_6)$alkylcarbonyloxy group or $(C_1-C_4)$alkoxycarbonyl group, or $(C_2-C_4)$alkenyl group, can be further obtained by reacting a corresponding halide of the formula (IIa):

$$X—R^{11} \qquad (IIa)$$

wherein
X represents a halogen atom and $R^{11}$ have the same meaning as defined above, such as cyanogen bromide, propyl bromide, halogenomethylthio halide, allyl bromide, etc. with a hydrazine derivative of the formula (Ia) (a hydrazine derivative of the formula (I) wherein $R^{11}$ is a hydrogen atom):

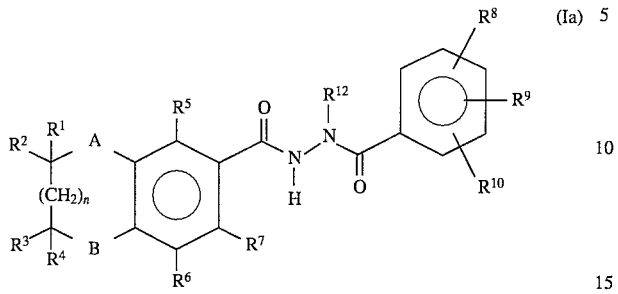 (Ia)

wherein $R^1$ to $R^{10}$ $R^{12}$ A, B and n are the same as defined above, in an inert solvent such as tetrahydrofuran, dioxane, ether, N,N'-dimethylformamide, dimethyl sulfoxide etc. in the presence of a base such as an alkali metal hydride (sodium hydride, etc.), preferably at −10° to 50° C.

The hydrazide of the formula (IIb):

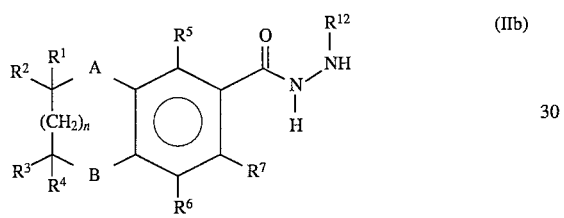 (IIb)

wherein

A, B, $R^1$ to $R^7$, $R^{12}$ and n are the same as defined above, which is used for preparing the hydrazine derivative of the formula (I) can be obtained by reacting a hydrazine represented by the formula (V):

$$R^{12}-NHNH_2 \cdot HCl \qquad (V)$$

wherein $R^{12}$ is the same as defined above, with a corresponding benzoyl halide represented by the formula (IV):

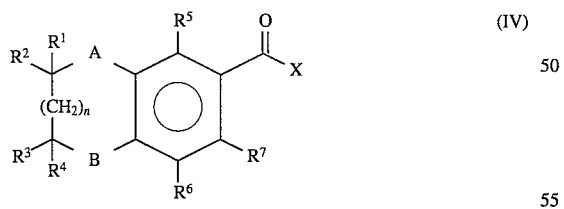 (IV)

wherein

A, B, $R^1$, $R^2$, $R^3$, $R^4$, $R^5$, $R^6$, $R^7$, and n have the same meanings as defined above, and X is a halogen atom.

The reaction conditions such as a solvent, reaction temperature, etc. are the same as those mentioned in the reaction of the hydrazide of the formula (II) and the benzoyl halide of the formula (III).

The hydrazide of the formula (IIb) can be further obtained by a known procedure, that is, reacting a compound of the formula (VI):

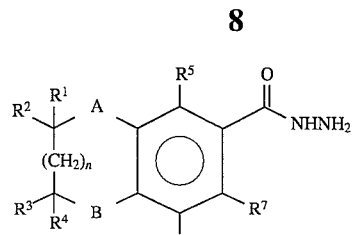 (VI)

wherein

A, B, $R^1$, $R^2$, $R^3$, $R^4$, $R^5$, $R^6$, $R^7$ and n have the same meanings as defined above, with an aldehyde of the formula (VII):

 (VII)

wherein $R^{15}$ is hydrogen atom or alkyl group and $R^{16}$ is an alkyl group, the total carbon number of $R^{15}$ and $R^{16}$ being 2 to 9, in a solvent such as alcohol (methanol, ethanol, etc.), hydrocarbon (toluene, benzene, etc.) and ether (tetrahydrofuran etc.), optionally in the presence of an organic acid such as acetic acid and trifluoroacetic acid to obtain a product of the formula (VIII):

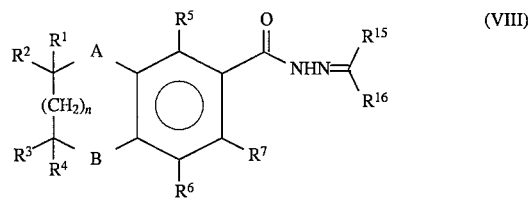 (VIII)

wherein

A, B, $R^1$, $R^2$, $R^3$, $R^4$, $R^5$, $R^6$, $R^7$, $R^{15}$, $R^{16}$ and n have the same meanings as defined above, and then reducing the product of the formula (VIII) with a reducing agent such as sodium cyanoborohydride, sodium borohydride and lithium aluminum hydride, optionally in the presence of a catalyst such as acetic acid and trifluoroacetic acid in an inert solvent such as alcohols and ethers.

The compound of the formula (Ia) can be obtained by reacting the benzoyl halide represented by the formula (IV):

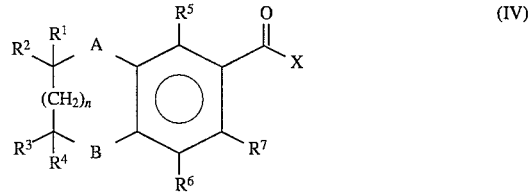 (IV)

wherein

A, B, $R^1$, $R^2$, $R^3$, $R^4$, $R^5$, $R^6$, $R^7$, and n have the same meanings as defined above, and X is a halogen atom, with a hydrazide represented by the formula (IX):

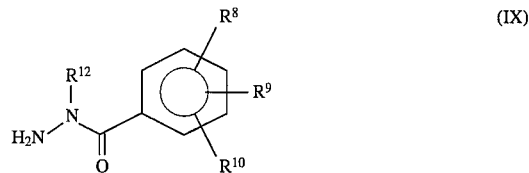 (IX)

wherein $R^8$, $R^9$, $R^{10}$, and $R^{12}$ have the same meanings as defined above. The reaction conditions such as a solvent, reaction temperature, etc. are the same as those employed in the reaction of the hydrazide of the formula (II) and the benzoyl halide of the formula (III).

The reaction mixture when preparing the hydrazine derivative of the formula (I) or the hydrazide of the formula (II) is stirred for a sufficient time, and after usual treatments such as extraction, washing with water, drying, removal of the solvent, etc., a desired compound can be recovered. In many cases, simple washing with a solvent may be sufficient, but if necessary, recrystallization or purification by column chromatography may be carried out.

The hydrazine derivative of the formula (I) may be used as it is or as a composition in the form of various formulation such as powder, fine powder, granule, wettable powder, flowable agent, emulsifiable concentrate, microcapsule, oily agent, aerosol, heat fumigant such as mosquito-repellent incense, electric mosquito-repellent, etc., haze agent such as fogging, etc., non-heat fumigant, a poison bait, etc., according to the method generally employed in the field of pesticide formulation by using the hydrazine derivative only or mixing a pesticide adjuvant in order to enhance or stabilize the pesticidal activity depending on the use and object.

These various formulations may be used without or after diluting with water to a desired concentration for practical use.

As the pesticide adjuvant herein mentioned, there may be mentioned a carrier (a diluent) and other adjuvant such as a spreader, an emulsifier, a humectant, a dispersant, a sticking agent, a disintegrator, etc. As a liquid carrier, there may be mentioned aromatic hydrocarbons such as toluene, xylene, etc., alcohols such as butanol, octanol, glycol, etc., ketones such as acetone, etc., amides such as dimethylformamide, etc., sulfoxides such as dimethylsulfoxide, etc., methylnaphthalene, cyclohexanone, animal and vegetable oils, fatty acids, fatty acid esters, petroleum fractions such as kerosene, light oil, etc., and water.

As a solid carrier, there may be mentioned clay, kaolin, talc, diatomaceous earth, silica, calcium carbonate, montmorillonite, bentonite, feldspar, quartz, alumina, sawdust, etc.

Also, as the emulsifier or dispersant, a surfactant is usually used and there may be mentioned anionic surfactants, cationic surfactants, nonionic surfactants and amphoteric surfactants such as higher alcohol sodium sulfate, stearyltrimethylammonium chloride, polyoxyethylene alkyl phenyl ether, lauryl betain, etc.

Also, as the spreader, there may be mentioned polyoxyethylene nonyl phenyl ether, polyoxyethylene lauryl ether, etc., as the humectant, there may be mentioned polyoxyethylene nonyl phenyl ether dialkylsulfosuccinate, etc., as the sticking agent, there may be mentioned carboxymethylcellulose, polyvinyl alcohol, etc., and as the disintegrator, there may be mentioned sodium lignin sulfonate, sodium laurylsulfate, etc.

Further, two or more of the hydrazine derivative of the present invention can be combinedly formulated to exhibit more excellent pesticidal effect. Also, a multipurpose pesticidal composition having further excellent effects can be prepared by mixing other physiologically active substance such as pyrethroids including aleslin, phthalthrin, permeslin, deltameslin, fenvalerate, cycloprothrin, etc. and various isomers thereof; pyrethrum extract; organophosphorus pesticide including DDVP (dichlorvos), fenitrothion, diazinon, temephos, etc.; carbamate pesticide including NAC (carbaryl), PHC (propoxur), BPMC (Fenbucarb), pirimicarb, carbosulfun, etc.; other pesticides; acaricides; fungicides; nematicides; herbicide; plant growth regulator; fertilizers; BT agents; insect hormones; and other agricultural chemicals. By mixing such substances, synergistic effects can be also expected.

Further, by mixing a known synergist of pyrethrin such as piperonyl butoxide, sulfoxide, saphroxane, NIA-16824 (O-sec-butyl O-propargyl phenylphosphonate), DEF (s,s,s-tributylphosphotrithioate), etc., the pesticidal effect of the hydrazine derivative can be enhanced.

The hydrazine derivative of the present invention has high stability to light, heat, oxidation, etc., but depending on necessity, antioxidants or UV-absorbers such as phenols including BHT, BHA, etc., arylamines such as α-naphthylamine and benzophenone compounds may be mixed as a stabilizer to obtain a composition having more stable effects.

The amount of the effective ingredient (the hydrazine derivative) in the pesticidal composition of the present invention may vary depending on formulation, method of application and other conditions, and the hydrazine derivative alone may be used in some case, but generally in the range from 0.02 to 95% by weight, preferably 0.05 to 80% by weight.

The application amount of the pesticidal composition of the present invention may vary depending on the formulation, method or time of application and other conditions, but for agricultural and horticultural purpose and for controlling pest in forest, field, garden and post harvest, the pesticidal composition may be applied 0.5 to 300 g, preferably 2 to 200 g per 10 ares based on the amount of the effective ingredient. Also, in case of controlling sanitary insect pest, the application amount of the pesticidal composition is usually in the range from 1 to 200 mg, preferably 1 to 100 mg per 1 $m^2$ based on the amount of the effective ingredient. For example, from 1 to 120 g per 10 ares for a powder agent, from 5 to 300 g per 10 ares for a granule, from 0.5 to 100 g for an emulsifiable concentrate, wettable powder, flowables, water dispersible granules and emulsion in water, all based on the amount of the effective ingredient. However, in a specific case, it may exceed or lower the above ranges and is necessary in some cases.

Also, when the hydrazine derivative of the formula (I) according to the present invention is used for controlling parasite, it may be used with an administration dose from 0.1 to 200 mg/kg based on the body weight. An accurate administration dose to the given state can be daily determined depending on various factors such as a hydrazine derivative to be used, kinds of parasite, kinds of formulation to be used and conditions of human or animal suffering from parasitic disease.

Specific harmful pests to which the pesticidal composition of the present invention can be applied are mentioned below.

Hemiptera: *Nephotettix cincticeps, Sogatella furcifera, Nilaparvata lugens, Laodelphax striatellus, Riptortus clavatus, Nezara viridula, Stephanitis nashi, Trialeurodes vaporariorum, Aphis gassypii, Myzus persicae, Unasqis yanonensis*

Lepidoptera: *Phyllonorycter ringoneella, Plutella xylostella, Promalactis inonisema, Adoxophyes orana, Leguminivora glycinivorella, Cnaphalocrocis medinalis, Chilo supperessalis, Ostrinia furnacalis, Mamestra brassicae, Pseudaletia separata, Spodoptera litura, Parnara guttata, Pieris rapae-crucivora,* Heliothis spp., Agrotis spp., Helicoverpa spp.

Coleoptera: *Anomala cuprea, Popillia japonica, Echinocnemus soqameus, Lissorhoptrus oryzophilus, Oulema oryzae, Anthrenus verbasic, Tenebroides mauritanicus, Sitophilus zeamis, Henosepilachna vigintioctopunctata, Callosobruchus chinensis, Monochamus alternatus, Aulacophora femoralis, Leptiontarsa decemlineta, Phaedon cochlearias,* Diabrotica spp.

Hymenoptera: *Athalia rosae japonensis, Argesimilis*
Diptera: *Culex pipiens fatigans, Aedes aegypti,* Asphondylls sp., *Hylemya platura, Musca domestica viclna, Dacus cucurcitae, Agromyza oryzae,* Lucllia spp. Aphaniptera, there may be mentioned *Pulex irritans, Xenosylla cheopis, Ctenocephalides canis* Thysanoptera, there may be mentioned *Scirtothrips dorsalls, Thrips tabaci, Thrips palmi, Baliothrips biformis*
Anoplura: *Pediculs humanus corporis, Pthirus pubis*
Psocoptera: *Trogium pulsatorium, Liposcelis bostrychophilus*
Orthoptera: *Gryllotalpa africana, Locusta migratoria, Oxya yezoensis, Blattella germanlica, Periplaneta fuliginosa.*

Also, the most general parasite which damages human and the diseases caused by them to which the pesticidal composition of the present invention can be applied are summarized below but the application of the present invention is not limited by these.

| Name of disease | Parasite |
| --- | --- |
| Bilharziosis or Schistosomiasis | *Schistosoma mansoni, S. Japonicum, S. Haematobium* |
| Ancyclostomiasis | *Necator americanus, Ancyclostoma duodenale* |
| Ascariasis | *Ascaris lumbricoldes* |
| Filariasis or elephantiasis | *Wuchereria bancrofti, Brugia malayi* |
| Onchoceriasis or river blinduess | *Onchocerrca volvulus, Loa loa* |
| Loiasis | |

In the following, the present invention is described in more detail by referring to examples, but the present invention is not limited by these examples.

Synthetic Example 1

Production of N-(5-methyl-1,4-benzodioxan-6-carbonyl)-N'-(1,2,2-trimethylpropyl)hydrazine:

In 10 ml of methanol, was dissolved 0.37 g of N-5-methyl- 1,4-benzodioxan-6-carbohydrazide, and a catalytic amount of acetic acid was added thereto and 0.20 g of pinacolone was added dropwise to the mixture. After stirring at room temperature for 3 hours, 0.21 g of acetic acid and 0.22 g of sodium cyano boron hydride were successively added to the mixture and the mixture was stirred at room temperature for 8 hours. The reaction mixture was poured into a 5% aqueous sodium hydroxide solution, and methanol was removed under reduced pressure and the residue was extracted by ethyl acetate. The ethyl acetate layer was washed successively with a diluted sodium hydroxide aqueous solution, water and then saturated saline solution, dried over anhydrous magnesium sulfate, and the solvent was removed under reduced pressure to obtain 0.47 g (yield: 90%)of the titled N-5-methyl-4-benzodioxan-6-carbonyl-N'- 1,2,2-trimethylpropylhydrazine.

$^1$H-NMR (CDCl$_3$) δ (ppm): 0.98 (9H, s), 1.07 (3H, d, J=6.6Hz), 2.27 (3H, s), 2.74 (1H, q, J=6.6 Hz), 4.26 (4H, s), 6.68 (1H, d, J=8.2 Hz), 6.87 (1H, d, J=8.2 Hz), 7.80 (1H, brs)

Synthetic Example 2

Production of N-5-methyl-1,4-benzodioxan-6-carbohydrazine:

In 4 ml of thionyl chloride, was dissolved 0.53 g of 5-methyl-1,4-benzodioxan-6-carboxylic acid and the solution was refluxed under heating for one hour. Excessive thionyl chloride was distilled off and the residue was dissolved in 3 ml of methylene chloride. To a mixed solution of 10 ml of methylene chloride and 2 ml of water, was added 1.4 g of hydrazine hydrate, and the previously prepared methylene chloride solution of 5-methyl-1,4-benzodioxan-6-carbonyl chloride was added dropwise to the mixture under cooling with ice.

After returned to room temperature and stirring for one hour, the mixture was poured into water and extracted with methylene chloride. The methylene chloride layer was washed successively with water and saturated saline solution, dried over anhydrous magnesium sulfate, condensed under reduced pressure to obtain 0.41 g (yield: 72%) of the titled N-5-methyl-1,4-benzodioxan-6-carbohydrazine.

$^1$H-NMR (CDCl$_3$) δ (ppm): 2.28 (3H, s), 3.74 (2H, brs), 4.27 (4H, s), 6.71 (1H, d, J=8.3 Hz), 6.92 (1H, d, J=8.3 Hz)

Synthetic Example 3

Production of N-(5-methyl-1,4-benzodioxan-6-carbonyl)-N'-(1,2,2-trimethylpropyl)-N'-(3,5-dimethylbenzoyl) hydrazine (Example No. 1–2)

In 8 ml of pyridine, was dissolved 0.43 g of N-5-methyl-1,4-benzodioxan-6-carbonyl-N'-1,2,2-trimethylpropyl-hydrazine and a catalytic amount of 4-dimethylaminopyridine (DMAP)was added to the solution, and 0.27 g of 3,5-dimethylbenzoyl chloride was added dropwise under cooling with ice.

After stirring at room temperature for 4 hours, the mixture was poured into water and extracted with ethyl acetate. The ethyl acetate layer was washed successively with a 5% hydrochloric acid, water and saturated saline solution, dried over anhydrous magnesium sulfate, and the solvent was removed under reduced pressure. The resulting crystals were recrystallized from a mixed solvent of ethyl acetate and diethyl ether to obtain 0.48 g of the titled N-5-methyl-1,4-benzodioxan-6-carbonyl-N'-1,2,2-trimethylpropyl-N'- 3,5-dimethylbenzoylhydrazine (yield: 78%).

$^1$H-NMR (CDCl$_3$) δ (ppm): 1.04 (9H, s), 1.29 (3H, d, J=6.3 Hz), 2.29 (9H, s), 4.22 (4H, s), 4.92 (1H, q, J=6.3 Hz), 6.28 (1H, d, J=8.2 Hz), 6.61 (1H, d, J=8.2 Hz), 7.00–7.12 (4H, m)

Synthetic Example 4

Production of N-(5-methyl-1,4-benzodioxan-6-carbonyl)-N'-t-butyl-N'-(3,5-dimethylbenzoyl)hydrazine (Example No. 1–5)

In 15 ml of pyridine, were dissolved 0.83 g of N-t-butyl-N'- 3,5-dimethylbenzoylhyrazine and a catalytic amount of DMAP and after cooling the solution to 0° C., 0.80 g of 5-methyl- 1,4-benzodioxan-6-carbonyl chloride was added dropwise to the solution. After stirring for 2 hours, water was added to the mixture and the mixture was extracted with ethyl acetate. The resulting ethyl acetate layer was washed successively with a 5% hydrochloric acid, water and saturated saline solution, dried over anhydrous magnesium sulfate, and the solvent was removed under reduced pressure. The resulting crystals were recrystallized from a mixed solvent of ethyl acetate and diethyl ether to obtain 0.61 g of the titled N-5-methyl 1,4-benzodioxan-6-carbonyl-N'-t-butyl-N'-3,5-dimethylbenzoylhydrazine (yield: 46%).

$^1$H-NMR (CDCl$_3$) δ (ppm): 1.58 (9H, s), 1.94 (3H, s), 2.25 (6H, s), 4.21 (4H, s), 6.12 (1H, d, J=8.3 Hz), 6.52 (1H, d, J=8.3 Hz), 6.98 (1H, s), 7.04 (2H, s), 7.50 (1H, brs).

Synthetic Example 5

Production of 5-methyl-1,4-benzodioxane

In 300 ml of dry dimethylformamide, was dissolved 30 g of 3-methylcatechol and then 100 g of potassium carbonate was added to the solution. This solution was heated to 120 to 130° C. and 136 g of 1,2-dibromoethane was added dropwise in ten and several portions. After stirring for 30 minutes under the same conditions, the mixture was cooled and solid materials were removed by filtration. To the filtrate, was added diethyl ether, and the mixture was washed successively with a 3% sodium hydroxide aqueous solution, water and saturated saline solution, dried over anhydrous magnesium sulfate, and the solvent was removed under reduced pressure. The resulting oily material was purified by silica gel column chromatography to obtain 29.7 g of the titled 5-methyl-1,4-benzodioxane (yield: 82%).

$^1$H-NMR (CDCl$_3$) δ (ppm): 2.19 (3H, s), 4.24 (4H, s), 6.71 (3H, s)

Synthetic Example 6

Production of 6-bromo-5-methyl-1,4-benzodioxane

In 30 ml of acetic acid, was dissolved 10 g of 5-methyl-1,4-benzodioxane and 11.8 g of bromine was added dropwise to the solution. After stirring for 30 minutes, the reaction mixture was poured into a sodium hydrogen sulfite aqueous solution and extracted with diethyl ether. The resulting diethyl ether layer was washed successively with a sodium hydrogen carbonate aqueous solution, water and saturated saline solution, dried over anhydrous magnesium sulfate, and the solvent was removed under reduced pressure to obtain 15.0 g of 6-bromo-5-methyl-1,4-benzodioxane (bp. 126°–135° C. (7 mmHg)).

$^1$H-NMR (CDCl$_3$) δ (ppm): 2.25 (3H, s), 4.23 (4H, s), 6.60 (1H, d, J=8.9 Hz), 6.99 (1H, d, J=8.9 Hz)

Synthetic Example 7

Production of 5-methyl-1,4-benzodioxan-6-carboxylic acid:

In 300 ml of dry tetrahydrofuran, was dissolved 32.0 g of 6-bromo-5-methyl-1,4-benzodioxane and after cooling the solution to −78° C., 96.7 ml of n-butyl lithium (n-hexane solution) was added dropwise over 20 minutes or more. After stirring at the same temperature for 1.5 hours, the reaction mixture was poured onto crushed dry ice and dry ice was sublimated while stirring. Water was added to the -mixture and the tetrahydrofuran was removed under reduced pressure. The resulting alkaline aqueous solution was washed with methylene chloride and adjusted to pH 3 with a 5% hydrochloric acid, and the precipitated crystals were collected by filtration and dried to obtain 20.9 g of 5-methyl-1,4-benzodioxan-6-carboxylic acid (yield: 77%).

$^1$H-NMR (CDCl$_3$) δ (ppm): 2.51 (3H, s), 4.29 (4H, s), 6.76 (1H, d, J=9.9 Hz), 7.62 (1H, d, J=9.9 Hz), 11.98 (1H, brs)

Synthetic Example 8

Production of 5-methyl-1,4-benzodioxan-6-carbaldehyde

In 100 ml of dry tetrahydrofuran, was dissolved 3.3 g of N,N,N'-trimethylethylenediamine and to the solution was added dropwise 19.2 ml of n-butyl lithium (1.59 mol/l, n-hexane solution) at −20° C. After stirring at −20° C. for 15 minutes, to the mixture was added dropwise 5.0 g of 1,4-benzodioxan- 6-carbaldehyde dissolved in 7 ml of dry tetrahydrofuran and the mixture was stirred for 15 minutes. Then, 57.5 ml of n-butyl lithium (1.59 mol/l, n-hexane solution)was further added dropwise to the mixture and the mixture was stirred at −20° C. for 3 hours. Thereafter, the mixture was cooled to −42° C. and 25.9 g of methyl iodide was added dropwise, and the mixture was stirred at the same temperature for 4 hours and poured into an ice-cooled 5% hydrochloric acid. The tetrahydrofuran was removed under reduced pressure and the mixture was extracted with diethyl ether, and the resulting diethyl ether layer was washed successively with water and saturated saline solution, and dried over anhydrous magnesium sulfate.

The solvent was removed under reduced pressure and the resulting oily material was purified by silica gel column chromatography to obtain 0.8 g of the titled 5-methyl-1,4-benzodioxan- 6-carbaldehyde (yield: 15%).

$^1$H-NMR (CDCl$_3$) δ (ppm): 2.52 (3H, s), 4.31 (4H, s), 6.83 (1H, d, J=8.5 Hz), 7.35 (1H, d, J=8.5 Hz), 10.10 (1H, s)

Synthetic Example 9

Production of 5-methyl-1,4-benzodioxan-6-carboxylic acid

In 5 ml of tetrahydrofuran was dissolved 0.8 g of 5-methyl- 1,4-benzodioxan-6-carbaldehyde, then 27 ml of a 1% sodium hydroxide aqueous solution was added dropwise to the solution and further 0.5 g of a 10% palladium-carbon was added thereto, and the mixture was refluxed under heating for 1.5 days. The mixture was cooled to room temperature, 10 ml of a 10% sodium sulfite aqueous solution was added thereto and after stirring for 30 minutes, the mixture was filtered and the tetrahydrofuran was removed under reduced pressure. The residue was adjusted to pH 3 with a 5% hydrochloric acid and extracted with diethyl ether. The diethyl ether layer was washed successively with water and saturated saline solution and dried over anhydrous magnesium sulfate. The solvent was removed under reduced pressure to obtain 0.53 g of the titled 5-methyl-1,4-benzodioxan- 6-carboxylic acid (yield: 61%).

$^1$H-NMR (CDCl$_3$) δ (ppm): 2.51 (3H, s), 4.29 (4H, s), 6.76 (1H, d, J=8.6 Hz), 7.62 (1H, d, J=8.6 Hz), 11.98 (1H, brs)

Synthetic Example 10

Production of N-5-methylchroman-6-carbonyl-N'-t-butylhydrazine:

In toluene, was suspended 3.3 g of 5-methylchroman-6-carboxylic acid and to the suspension were added 2.5 ml of thionyl chloride and a catalytic amount of N,N-dimethylformamide, and the mixture was stirred at 80° C. for 2 hours. The excessive thionyl chloride and the toluene were removed by distillation, and the residue was dissolved in 10 ml of methylene chloride. To 30 ml of a methylene chloride solution containing 6.4 g of t-butylhydrazine hydrochloride, was added 34 g of a 10% sodium hydroxide aqueous solution under cooling with ice and to the mixture was further added dropwise the previously prepared methylene chloride solution of 5-methylchroman-6-carbonyl chloride. After stirring for 30 minutes, the mixture was poured into water and extracted with methylene chloride. The methylene chloride layer was washed with saturated saline solution and dried over anhydrous magnesium sulfate. The solvent was removed under reduced pressure and the residue obtained was washed with diethyl ether to obtain 3.7 g of the titled N-5-methylchroman-6-carbo-N'-t-butylhydrazine (yield: 82%).

$^1$H-NMR (CDCl$_3$) δ (ppm): 7.12 and 6.65 (d, 2H), 5.60 (brs, 2H), 4.14 (t, 2H), 2.66 (t, 2H), 2.29 (s, 3H), 2.04 (q, 2H), 1.16 (s, 9H)

Synthetic Example 11

Production of
N-(5-methylchroman-6-carbonyl)-N'-t-butyl-N'-(3,5-dimethylbenzoyl)hydrazine (Example No. 1–15)

In 20 ml of pyridine, was dissolved 3.7 g of N-5-methylchroman-6-carbo-N'-t-butylhydrazine and to the solution was added a catalytic amount of 4-dimethylaminopyridine, and then 2.85 g of 3,5-dimethylbenzoyl chloride was added dropwise to the mixture under cooling with ice. After stirring at room temperature for 2 hours, the mixture was poured into water and extracted with ethyl acetate. The ethyl acetate layer was washed with a 5% hydrochloric acid and saturated saline solution, and dried over anhydrous magnesium sulfate. The solvent was removed under reduced pressure and the resulting crystals were washed with diethyl ether to obtain 5.0 g of the titled N-5-methylchroman-6-carbonyl-N'-t-butyl-N'-3,5-dimethylbenzoylhydrazine (yield: 90%).

$^1$H-NMR (CDCl$_3$) δ (ppm): 7.43 (s, 1H), 7.05 and 6.98 (bs, 3H), 6.44 and 6.37 (d, 2H), 4.15 (t, 2H), 2.56 (t, 2H), 2.26 (s, 6H), 1.98 (m, 2H), 1.95 (s, 3H), 1.59 (s, 9H)

Synthetic Example 12

Production of
N-cyano-N-(5-methyl-1,4-benzodioxan-6-carbonyl)-N'-t-butyl-N'-(3,5-dimethylbenzoyl)hydrazine (Example No. 1–139)

A solution of N-5-methyl-1,4-benzodioxan-6-carbonyl-N'-t-butyl-N'- 3,5-dimethylbenzoylhydrazine (300 mg) in tetrahydrofuran (6 ml) was treated slowly with 60% sodium hydride (50 mg) at room temperature. After 15 minutes, a solution of cyanogen bromide (135 mg) in tetrahydrofuran (2 ml) was added dropwise, the reaction mixture was refluxed for 1 hr, poured into cold water, and then extracted with ethyl ether. The organic layer was washed with water and saturated aqueous NaCl. After the extracts were dried over anhydrous magnesium sulfate, evaporation of solvents gave an oil which was chromatographed on silica gel to give 256 mg of N-cyano-N-(5-methyl-1,4-benzodioxan-6-carbonyl)-N'-t-butyl-N'-(3, 5-dimethylbenzoyl)hydrazine as a pale yellow crystal.

$^1$H-NMR (CDCl$_3$) δ (ppm): 1.69 (9H, s), 1.84 (3H, s), 2.31 (6H, s), 4.22–4.27 (4H, m), 6.10 (1H, d, J=8.5 Hz), 6.59 (1H, d, J=8.5 Hz), 7.08 (1H, s), 7.13 (2H, s)

Synthetic Example 13

Production of
N-(dimethylcarbamoyl)-N-(5-methyl-1,4-benzodioxan-6-carbo)-N'-t-butyl-N'-(3,5-dimethylbenzoyl)hydrazine (Example No. 1–84)

To a suspension of 60% sodium hydride (428 mg) in dimethylformamide (15 ml) at room temperature was added dropwise a solution of N-(5-methyl-1,4-benzodioxan-6-carbo)-N'-t-butyl-N'-3,5-dimethylbenzoylhydrazinde (1.01 g) in dimethylformamide (5 ml). The resulting suspension was stirred at room temperature for 30 min, and dimethylcarbamoyl chloride (0.94 ml) was added and stirred at room temperature for 15 min, and then stirred at 100° C. for 2 hrs.

The reaction mixture was poured into cold water, and then extracted with ethyl acetate. The organic layer was washed with water and saturated aqueous NaCl. After the extracts were dried over anhydrous magnesium sulfate, evaporation of the solvents gave an oil which was chromatographed on silica gel to give 225 mg of N-(dimethylcarbamoyl)-N-(5-methyl-1,4-benzodioxan-6-carbonyl)-N'-t-butyl-N'-(3,5-dimethylbenzoyl)hydrazine as a solid (mp=60°–64° C.).

$^1$H-NMR (CDCl$_3$) δ (ppm): 1.56 (9H, s), 2.24 (3H, s), 2.36 (6H, s), 2.55–2.75 (3H, brs), 2.80–3.05 (3H, brs), 4.20–4.27 (4H, m), 6.61 (1H, d, J=8.4 Hz), 7.12 (1H, s), 7.21 (1H, d, J=8.4 Hz), 7.66 (2H, s)

Representative examples of the hydrazine derivative according to the present invention are shown in the following tables.

TABLE 1

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-1 | O | O | H | H | H | H | Me | H | H | 2'-Cl | H | 5'-Me | H | —CMe₃ | 237–238 |
| 1-2 | O | O | H | H | H | H | Me | H | H | H | 3'-Me | 5'-Me | H | —CH(CMe₃)—Me | 237–238 |
| 1-3 | O | O | H | H | H | H | Me | H | H | H | H | H | H | —CMe₃ | 189–192 |
| 1-4 | O | O | H | H | H | H | Me | H | H | 2'-I | H | H | H | —CMe₃ | 215–216 |
| 1-5 | O | O | H | H | H | H | Me | H | H | H | 3'-Me | 5'-Me | H | —CMe₃ | 129–131 |
| 1-6 | O | O | H | H | H | H | Me | H | H | 2'-Cl | H | 5'-Me | H | —CH(CMe₃)—Me | 179–180 |
| 1-7 | O | O | H | H | H | H | Me | H | H | H | 3'-Me | H | H | —CH(CMe₃)—Me | 172–174 |
| 1-8 | O | —CH₂— | H | H | H | H | Me | H | H | H | 3'-Me | 5'-Me | H | —CMe₃ | 124–126 |
| 1-9 | O | O | H | H | H | H | Br | H | H | H | 3'-Me | 5'-Me | H | —CMe₃ | 274–275 |

TABLE 2

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-10 | O | O | H | H | H | H | NO₂ | H | H | H | 3'-Me | 5'-Me | H | —CMe₃ | 224–225 |
| 1-11 | O | O | H | H | H | H | NH₂ | H | H | H | 3'-Me | 5'-Me | H | —CMe₃ | 226–227 |
| 1-12 | O | CH₂ | Me | Me | H | H | Me | H | H | H | 3'-Me | 5'-Me | H | —CMe₃ | 118–120 |
| 1-13 | O | O | H | H | H | H | Me | H | H | 2'-Cl | 4'Cl | H | H | —CMe₃ | Amorphous |
| 1-14 | O | O | H | H | H | H | Me | H | H | H | 3'-Me | 5'-CH₂OSi(Me)(Me)—Bu(t) | H | —CMe₃ | Amorphous |
| 1-15 | CH₂ | O | H | H | H | H | Me | H | H | H | 3'-Me | 5'-Me | H | —CMe₃ | 114–116 |
| 1-16 | CH₂ | O | H | H | Me | Me | Me | H | H | H | 3'-Me | 5'-Me | H | —CMe₃ | 125–127 |
| 1-17 | O | O | H | H | H | H | F | H | H | H | 3'-Me | 5'-Me | H | —CMe₃ | 234–235 |
| 1-18 | —C(=O)— | O | H | H | H | H | H | H | H | H | 3'-Me | 5'-Me | H | —CMe₃ | 247–248 |
| 1-19 | O | O | H | H | H | H | Me | H | H | 2'-NO₂ | H | H | H | —CMe₃ | Amorphous |
| 1-20 | O | O | H | H | H | H | Me | H | H | H | 3'-Me | 5'-CH₂OH | H | —CMe₃ | 127–129 |
| 1-21 | O | O | H | H | H | H | Me | H | H | H | 3'-Cl | 5'-Cl | H | —CMe₃ | 254–256 |
| 1-22 | O | O | H | H | H | H | Me | H | H | H | 3'-Me | 5'-CHO | H | —CMe₃ | 203–205 |
| 1-23 | O | O | H | H | H | H | Me | H | H | H | 3'-Me | 5'-CH₂F | H | —CMe₃ | 113–115 |

TABLE 3

| No. | A | B | $R^1$ | $R^2$ | $R^3$ | $R^4$ | $R^5$ | $R^6$ | $R^7$ | $R^8$ | $R^9$ |
|---|---|---|---|---|---|---|---|---|---|---|---|
| 1-24 | O | O | H | H | H | H | Me | H | H | H | 3'-Me |
| 1-25 | O | O | H | H | H | H | Me | H | H | 2'-$NO_2$ | H |
| 1-26 | O | O | H | H | H | H | Me | H | H | 2'-$NO_2$ | 3'-Me |
| 1-27 | O | O | H | H | H | H | Me | H | H | H | 3'-OMe |
| 1-28 | O | O | H | H | H | H | Me | H | H | 2'-Cl | 3'-Cl |
| 1-29 | O | O | H | H | H | H | Me | H | H | H | H |
| 1-30 | O | O | H | H | H | H | Me | H | H | 2'-$NO_2$ | 3'-Me |
| 1-31 | O | O | H | H | H | H | $CH_2Br$ | H | H | H | 3'-Me |
| 1-32 | O | O | H | H | H | H | $C_3H_7(i)$ | H | H | H | 3'-Me |
| 1-33 | O | O | H | H | H | H | H | $C_3H_7(i)$ | H | H | 3'-Me |
| 1-34 | O | O | H | H | H | H | Me | H | H | H | 3'-Me |
| 1-35 | $CH_2$ | O | H | H | H | H | Me | Cl | H | H | 3'-Me |
| 1-36 | $CH_2$ | O | H | H | H | H | Me | Me | H | H | 3'-Me |
| 1-37 | OMe–CH< | O | H | H | H | H | H | H | H | H | 3'-Me |

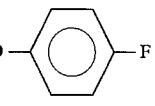

| No. | $R^{10}$ | $R^{11}$ | $R^{12}$ | Melting Point (°C.) |
|---|---|---|---|---|
| 1-24 | 5'-$CHF_2$ | H | $-CMe_3$ | 100–103 |
| 1-25 | 5'-Me | H | $-CMe_3$ | 212–214 |
| 1-26 | H | H | $-CMe_3$ | 165–168 |
| 1-27 | H | H | $-CMe_3$ | 92–95 |
| 1-28 | 5'-Cl | H | $-CMe_3$ | 201–204 |
| 1-29 | 3'-O—$CH_2CH_2$O—(phenyl)—F | H | $-CMe_3$ | 195–198 |
| 1-30 | 5'-Me | H | $-CMe_3$ | 202–203 |
| 1-31 | 5'-Me | H | $-CMe_3$ | 119–120 |
| 1-32 | 5'-Me | H | $-CMe_3$ | 158–160 |
| 1-33 | 5'-Me | H | $-CMe_3$ | 236-7 |
| 1-34 | 5'-Me | $-CH_2OC(=O)-Bu(t)$ | $-CH(Me)-CMe_3$ | Amorphous |
| 1-35 | 5'-Me | H | $-CMe_3$ | 204–207 |
| 1-36 | 5'-Me | H | $-CMe_3$ | 138–140 |
| 1-37 | 5'-Me | H | $-CMe_3$ | 203–204 |

TABLE 4

| No. | A | B | $R^1$ | $R^2$ | $R^3$ | $R^4$ | $R^5$ | $R^6$ | $R^7$ | $R^8$ | $R^9$ | $R^{10}$ | $R^{11}$ | $R^{12}$ | Melting Point (°C.) |
|---|---|---|---|---|---|---|---|---|---|---|---|---|---|---|---|
| 1-38 | OMe–CH< | O | H | H | H | H | H | H | H | H | 3'-Cl | 5'-Cl | H | $-CMe_3$ | 191-192 |
| 1-39 | O | O | H | H | H | H | Me | H | H | H | 3'-Me | 5'-Me | $-C(=O)-C(=O)-OEt$ | $-CH(Me)-CMe_3$ | Amorphous |
| 1-40 | O | O | H | H | H | H | Me | H | H | H | 3'-Cl | 5'-Cl | H | $-CH(Me)-CMe_3$ | 208–209 |
| 1-41 | O | O | H | H | H | H | Me | H | H | H | 3'-Me | 5'-CH=$CH_2$ | H | $-CMe_3$ | Amorphous |
| 1-42 | O | O | H | H | H | H | Me | H | H | H | 3'-Me | 5'-$C_2H_5$ | H | $-CMe_3$ | Amorphous |
| 1-43 | O | O | H | H | H | H | $CH_2F$ | H | H | H | 3'-Me | 5'-Me | H | $-CMe_3$ | 105–108 |
| 1-44 | O | O | H | H | H | H | $CHF_2$ | H | H | H | 3'-Me | 5'-Me | H | $-CMe_3$ | 186–189 |

TABLE 4-continued

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-45 | —CH—<br>　\|<br>　O<br>　\|<br>　CH₂<br>　\|<br>　(4-F-C₆H₄) | O | H | H | H | H | H | H | H | H | 3'-Me | 5'-Me | H | —CMe₃ | 193–194 |
| 1-46 | O | O | H | H | H | H | C₂H₅ | H | H | H | 3'-Me | 5'-Me | H | —CMe₃ | 108–111 |
| 1-47 | S | O | H | H | H | H | H | H | H | H | 3'-Me | 5'-Me | H | —CMe₃ | 250–252 |

TABLE 5

| No. | A | B | R¹ | R² | R³ | R⁴ | R⁵ |
|---|---|---|---|---|---|---|---|
| 1-48 | CH₂ | O | H | H | H | H | F |
| 1-49 | CH₂ | O | H | H | H | H | H |
| 1-50 | CH₂ | O | H | H | H | H | H |
| 1-51 | O | O | Me | H | H | H | Me |
| 1-52 | O | O | H | H | Me | H | Me |
| 1-53 | O | \C(=O)/ | H | H | H | H | Me |
| 1-54 | O | O | MeOCH₂— | H | H | H | Me |
| 1-55 | O | O | C₆H₅-CH₂OCH₂ | H | H | H | Me |
| 1-56 | O | O | H | H | H | H | Me |
| 1-57 | O | O | H | H | H | H | —CH=CH₂ |
| 1-58 | O | O | H | H | H | H | —CH₂SMe |
| 1-59 | O | O | H | H | H | H | Me |
| 1-60 | O | O | H | H | H | H | Me |
| 1-61 | O | O | H | H | H | H | Me |
| 1-62 | CH₂ | O | H | H | H | H | Me |

| No. | R⁶ | R⁷ | R⁸ | R⁹ | R¹⁰ | R¹¹ | R¹² | Melting Point (°C.) |
|---|---|---|---|---|---|---|---|---|
| 1-48 | H | H | H | 3'-Me | 5'-Me | H | —CMe₃ | 203–205 |
| 1-49 | F | H | H | 3'-Me | 5'-Me | H | —CMe₃ | |
| 1-50 | H | F | H | 3'-Me | 5'-Me | H | —CMe₃ | 174–175 |
| 1-51 | H | H | H | 3'-Me | 5'-Me | H | —CMe₃ | 128–13 |
| 1-52 | H | H | H | 3'-Me | 5'-Me | H | —CMe₃ | 203–205 |
| 1-53 | H | H | H | 3'-Me | 5'-Me | H | —CMe₃ | 201–203 |
| 1-54 | H | H | H | 3'-Me | 5'-Me | H | —CMe₃ | 124–126 |
| 1-55 | H | H | H | 3'-Me | 5'-Me | H | —CMe₃ | 196–198 |
| 1-56 | Br | H | H | 3'-Me | 5'-Me | H | —CMe₃ | Amorphous |
| 1-57 | H | H | H | 3'-Me | 5'-Me | H | —CMe₃ | 97–100 |
| 1-58 | H | H | H | 3'-Me | 5'-Me | H | —CMe₃ | 85–87 |
| 1-59 | H | H | 2'-NO₂ | H | 5'-Cl | H | —CMe₃ | 200–203 |
| 1-60 | Me | H | H | 3'-Me | 5'-Me | H | —CMe₃ | 122–124 |
| 1-61 | H | NO₂ | H | 3'-Me | 5'-Me | H | —CMe₃ | 222–224 |
| 1-62 | H | H | H | 3'-Cl | 5'-Cl | H | —CMe₃ | 193–195 |

TABLE 6

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-63 | $CH_2$ | O | H | H | H | H | Me | H | H | 3'-Me | 4'-F | 5'-Me | H | —$CMe_3$ | 216–218 |
| 1-64 | $CH_2$ | O | H | H | H | H | Me | H | H | 2'-Cl | H | 5'-Me | H | —$CMe_3$ | 217–220 |
| 1-65 | $CH_2$ | O | H | H | H | H | Me | H | H | 2'-Cl | 4'-F | 5'-Me | H | —$CMe_3$ | 190–191 |
| 1-66 | $CH_2$ | O | H | H | H | H | H | Me | H | H | 3'-Me | 5'-Me | H | —$CMe_3$ | Amorphous |
| 1-67 | O | O | H | H | H | H | Me | H | Cl | H | 3'-Me | 5'-Me | H | —$CMe_3$ | 133–134 |
| 1-68 | O | O | H | H | H | H | Me | Cl | H | H | 3'-Me | 5'-Me | H | —$CMe_3$ | Amorphous |
| 1-69 | O | O | H | H | H | H | —$CH_2OMe$ | H | H | H | 3'-Me | 5'-Me | H | —$CMe_3$ | 78–81 |
| 1-70 | O | O | H | H | H | H | CN | H | H | H | 3'-Me | 5'-Me | H | —$CMe_3$ | 264–266 |
| 1-71 | O | O | H | H | H | H | Me | H | H | 2'-$NO_2$ | 3'-Cl | H | H | —$CMe_3$ | 87–91 |
| 1-72 | O | O | H | H | H | H | —CH=CH—$CH_3$ | H | H | H | 3'-Me | 5'-Me | H | —$CMe_3$ | 95–99 |
| 1-73 | O | O | H | H | H | H | Pr(n) | H | H | H | 3'-Me | 5'-Me | H | —$CMe_3$ | 93–95 |
| 1-74 | $CH_2$ | O | H | H | H | H | Me | H | H | 2'-$NO_2$ | H | H | H | —$CMe_3$ | 212–214 |
| 1-75 | O | —CH—<br>\|<br>OMe | H | H | H | H | Me | H | H | H | 3'-Me | 5'-Me | H | —$CMe_3$ | 113–116 |
| 1-76 | O | O | H | H | H | H | Cl | H | H | H | 3'-Me | 5'-Me | H | —$CMe_3$ | 271–273 |
| 1-77 | O | O | H | H | H | H | OMe | H | H | H | 3'-Me | 5'-Me | H | —$CMe_3$ | 155–157 |

TABLE 7

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-78 | O | O | H | H | H | H | Me | H | Me | H | 3'-Me | 5'-Me | H | —$CMe_3$ | |
| 1-79 | O | O | H | H | H | H | H | H | Me | H | 3'-Me | 5'-Me | H | —$CMe_3$ | 240–242 |
| 1-80 | O | O | H | H | H | H | Me | H | F | H | 3'-Me | 5'-Me | H | —$CMe_3$ | 254–256 |
| 1-81 | O | O | F | F | F | F | Me | H | H | H | 3'-Me | 5'-Me | H | —$CMe_3$ | |
| 1-82 | O | O | H | H | H | H | Me | H | H | H | 3'-Me | 5'-Me | $COCH_3$ | —$CMe_3$ | Amorphous |
| 1-83 | O | O | H | H | H | H | Me | H | H | H | 3'-Me | 5'-Me | Me | —$CMe_3$ | 76–78 |
| 1-84 | O | O | H | H | H | H | Me | H | H | H | 3'-Me | 5'-Me | $CON(Me)_2$ | —$CMe_3$ | 60–64 |
| 1-85 | O | O | H | H | H | H | Me | H | H | H | 3'-Me | 5'-Me | $CH_2CH_2OEt$ | —$CMe_3$ | 92–94 |
| 1-86 | O | O | H | H | H | H | Me | H | H | H | 3'-Me | 5'-Me | $CH_2OEt$ | —$CMe_3$ | 65–68 |
| 1-87 | O | O | H | H | H | H | Me | H | H | H | 3'-Me | 5'-Me | $CH_2CH=CH_2$ | —$CMe_3$ | Amorphous |
| 1-88 | O | O | H | H | H | H | Me | H | H | H | 3'-Me | 5'-Me | $SCCl_3$ | —$CMe_3$ | Amorphous |
| 1-89 | O | O | H | H | H | H | Me | H | H | H | 3'-Me | 5'-Me | COOBu(iso) | —$CMe_3$ | Amorphous |
| 1-90 | O | O | H | H | H | H | Me | H | H | H | 3'-Me | 5'-Me | $CH_2CH_2CH_2Br$ | —$CMe_3$ | Amorphous |
| 1-91 | $CH_2$ | O | H | H | H | H | Me | H | H | H | 3'-Me | 5'-Me | $SCCl_3$ | —$CMe_3$ | 87–90 |
| 1-92 | O | O | H | H | H | H | Me | H | H | 3'-Me | 4'-F | 5'-Me | H | —$CMe_3$ | 245–246 |
| 1-93 | O | O | H | H | H | H | Me | H | H | 2'-Cl | 4'-F | 5'-Me | H | —$CMe_3$ | 133–135 |

TABLE 8

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-94 | O | O | H | H | H | H | Me | H | H | 2'-Br | 4'-F | H | H | —$CMe_3$ | 207–208 |
| 1-95 | O | O | H | H | H | H | Me | H | H | H | H | 3'-$OCF_3$ | H | —$CMe_3$ | 224–225 |
| 1-96 | O | O | H | H | H | H | Me | H | H | H | 3'-Me | 5'-OMe | H | —$CMe_3$ | 218–220 |
| 1-97 | O | O | H | H | H | H | Me | H | H | H | 3'-Me | 3'-C≡CH | H | —$CMe_3$ | 130–133 |
| 1-98 | O | O | H | H | H | H | Me | H | H | 2'-$SCF_3$ | H | H | H | —$CMe_3$ | 197–199 |
| 1-99 | O | O | H | H | H | H | Me | H | H | 2'-$CF_2$ | H | H | H | —$CMe_3$ | 212–213 |
| 1-100 | O | O | H | H | H | H | Me | H | H | H | 3'-Me | 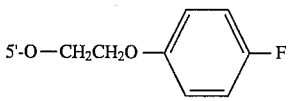 | H | —$CMe_3$ | 158–160 |

TABLE 8-continued

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-101 | O | O | H | H | H | H | Me | H | H | H | 3'-Me | 5'-O—CH₂CH₂O—C₆H₄—CF₃ 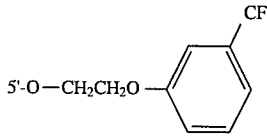 | H | —CMe₃ | 160–161 |
| 1-102 | O | O | H | H | H | H | Me | H | H | H | 3'-Me | 5'-O—CH₂CH₂O—C₆H₄—CH₃ 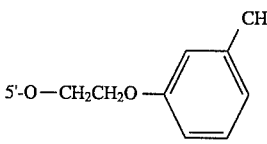 | H | —CMe₃ | Amorphous |
| 1-103 | O | O | H | H | H | H | Me | H | H | H | 3'-Me | 5'-OCH₂CH₂—C₆H₄—Cl 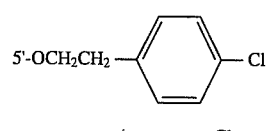 | H | —CMe₃ | 176–177 |
| 1-104 | O | O | H | H | H | H | Me | H | H | H | 3'-Me | 5'-OCH₂—C₆H₄—Cl 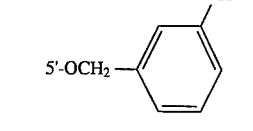 | H | —CMe₃ | 207–209 |
| 1-105 | O | O | H | H | H | H | Me | H | H | H | 3'-Me | 5'-OCH₂CF₃ | H | —CMe₃ | Amorphous |

TABLE 9

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-106 | —CH(Me)— | O | H | H | H | H | Me | H | H | H | 3'-Me | 5'-Me | H | —CMe₃ | |
| 1-107 | —C(=O)— | O | H | H | H | H | Me | H | H | H | 3'-Me | 5'-Me | H | —CMe₃ | 133–136 |
| 1-108 | —CH(OH)— | O | H | H | H | H | Me | H | H | H | 3'-Me | 5'-Me | H | —CMe₃ | 234–237 |
| 1-109 | —C(=N—OMe)— | O | H | H | H | H | Me | H | H | H | 3'-Me | 5'-Me | H | —CMe₃ | 236–240 |
| 1-110 | O | —CH(Me)— | H | H | H | H | Me | H | H | H | 3'-Me | 5'-Me | H | —CMe₃ | |
| 1-111 | —CH₂— | O | H | H | H | H | Me | H | H | 2'-Br | 4'-F | H | H | —CMe₃ | 208–209 |
| 1-112 | —CH₂— | O | H | H | H | H | Me | H | H | H | H | 4'-Bu(t) | H | —CMe₃ | 270–272 |
| 1-113 | —CH₂— | O | H | H | H | H | Me | H | H | H | H | 3'-OCF₃ | H | —CMe₃ | 197–200 |
| 1-114 | —CH₂— | O | H | H | H | H | Me | H | H | 2'-I | H | H | H | —CMe₃ | 237–239 |
| 1-115 | —CH₂— | O | H | H | H | H | Me | H | H | 2'-SCF₃ | H | H | H | —CMe₃ | 150–152 |
| 1-116 | —CH₂— | O | H | H | H | H | Me | H | H | H | H | 3'-CHO | H | —CMe₃ | 220–223 |
| 1-117 | —CH₂— | O | H | H | H | H | Me | H | H | H | 3'-Me | 5'-OMe | H | —CMe₃ | 110–115 |

TABLE 10

| No. | A | B | R¹ | R² | R³ | R⁴ | R⁵ | R⁶ | R⁷ | R⁸ | R⁹ |
|---|---|---|---|---|---|---|---|---|---|---|---|
| 1-118 | —CH$_2$— | O | H | H | H | H | Me | H | H | H | 3'-Me |
| 1-119 | —CH$_2$— | O | H | H | H | H | Me | H | H | H | 3'-Cl |
| 1-120 | —CH$_2$— | O | H | H | H | H | Me | H | H | 2'-Cl | 4'-Cl |
| 1-121 | —CH$_2$— | O | H | H | H | H | Me | H | H | 2'-NO$_2$ | H |
| 1-122 | —CH$_2$— | O | H | H | H | H | H | H | Me | H | 3'-Me |
| 1-123 | —CH$_2$— | O | H | H | H | H | Me | H | H | H | 3'-Me |
| 1-124 | —CH$_2$— | O | H | H | H | H | Me | H | H | H | 3'-Me |
| 1-125 | —CH$_2$— | O | H | H | H | H | Me | H | H | H | 3'-Me |
| 1-126 | —CH$_2$— | O | H | H | H | H | Me | H | H | H | 3'-Me |

| No. | R¹⁰ | R¹¹ | R¹² | Melting Point (°C.) |
|---|---|---|---|---|
| 1-118 | 5'-Me | H | —CH(Me)—CMe$_3$ | 179–180 |
| 1-119 | 5'-Cl | H | —CH(Me)—CMe$_3$ | 190–191 |
| 1-120 | H | H | —CH(Me)—CMe$_3$ | 113–116 |
| 1-121 | H | H | —CH(Me)—CMe$_3$ | Amorphous |
| 1-122 | 5'-Me | H | —CMe$_3$ | 202–204 |
| 1-123 | 5'-OCH$_2$CH$_2$O—C$_6$H$_4$—F | H | —CMe$_3$ | 137–139 |
| 1-124 | 5'-OCH$_2$CH$_2$O—C$_6$H$_4$(CF$_3$) | H | —CMe$_3$ | 158–160 |
| 1-125 | 5'-OCH$_2$CH$_2$O—C$_6$H$_4$(CH$_3$) | H | —CMe$_3$ | Amorphous |
| 1-126 | 5'-OCH$_2$CH$_2$O—C$_6$H$_4$—Cl | H | —CMe$_3$ | 169–171 |

TABLE 11

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-127 | —CH$_2$— | O | H | H | H | H | Me | H | H | H | 3'-Me | 5'-OCH$_2$—C$_6$H$_4$—Cl | H | —CMe$_3$ | 185–187 |
| 1-128 | —CH$_2$— | O | H | H | H | H | Me | H | H | H | 3'-Me | 5'-OCH$_2$CF$_3$ | H | —CMe$_3$ | Amorphous |

TABLE 11-continued

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 1-129 | Me<br>\|<br>—N— | O | H | H | H | H | H | H | H | H | 3'-Me | 5'-Me | H | —CMe₃ | 248–251 |
| 1-130 | Ac<br>\|<br>—N— | O | H | H | H | H | H | H | H | H | 3'-Me | 5'-Me | H | —CMe₃ | 232–235 |
| 1-131 | O | —N—<br>\|<br>Me | H | H | H | H | H | H | H | H | 3'-Me | 5'-Me | H | —CMe₃ | 249–250 |
| 1-132 | H<br>\|<br>—N— | O | H | H | H | H | H | H | H | H | 3'-Me | 5'-Me | H | —CMe₃ | 248–252 |
| 1-133 | O | —N—<br>\|<br>Ac | H | H | H | H | H | H | H | H | 3'-Me | 5'-Me | H | —CMe₃ | 120–122 |
| 1-134 | O | —N—<br>\|<br>H | H | H | H | H | H | H | H | H | 3'-Me | 5'-Me | H | —CMe₃ | 225–227 |
| 1-135 | O | O | H | H | H | H | CH₃ | H | H | 2'-F | H | H | H | —CMe₃ | 158–159 |
| 1-136 | O | O | H | H | H | H | CH₃ | H | H | H | 3'-Cl | 4'-Cl | H | —CMe₃ | 258–259 |
| 1-137 | O | O | H | H | H | H | CH₃ | H | H | H | 3'-CH₃ | 5'-CH₃ | H | —CH₂—CMe₃ | 182–184 |

TABLE 12

| No. | A | B | R¹ | R² | R³ | R⁴ | R⁵ | R⁶ | R⁷ | R⁸ | R⁹ |
|---|---|---|---|---|---|---|---|---|---|---|---|
| 1-138 | CH₂—CH₂<br>\\ /<br>O   O<br>\\/<br>C | O | H | H | H | H | CH₃ | H | H | H | 3'-CH₃ |
| 1-139 | O | O | H | H | H | H | CH₃ | H | H | H | 3'-CH₃ |
| 1-140 | O | O | H | H | H | H | CH₃ | H | H | H | 3'-CH₃ |
| 1-141 | O | O | H | H | H | H | CH₃ | Cl | Cl | H | 3'-CH₃ |
| 1-142 | O | O | H | H | H | H | CH₃ | H | Br | H | 3'-CH₃ |
| 1-143 | O | O | H | H | H | H | CH₃ | CHCl₂ | H | H | 3'-CH₃ |
| 1-144 | O | O | H | H | H | H | CH₃ | H | H | H | 3'-CH₃ |
| 1-145 | O | O | H | H | H | H | CH₃ | H | H | H | 3'-CH₃ |
| 1-146 | CH₂ | O | H | H | H | H | CH₃ | H | H | H | 3'-CH₃ |
| 1-147 | CH₂ | O | H | H | H | H | CH₃ | H | H | H | 3'-CH₃ |
| 1-148 | CH₂ | O | H | H | H | H | CH₃ | H | H | H | 3'-CH₃ |
| 1-149 | O | O | H | H | H | H | CH₃ | H | H | H | H |
| 1-150 | O | O | H | H | H | H | CH₃ | H | H | H | H |
| 1-151 | CH₂ | O | H | H | H | H | CH₃ | H | H | H | 3'-CH₃ |
| 1-152 | CH₂ | O | H | H | H | H | CH₃ | H | H | H | 3'-CH₃ |

| No. | R¹⁰ | R¹¹ | R¹² | Melting Point (°C.) |
|---|---|---|---|---|
| 1-138 | 5'-CH₃ | H | —CMe₃ | 243–244 |
| 1-139 | 5'-CH₃ | CN | —CMe₃ | 159–161 |
| 1-140 | 5'-CH₃ | O<br>‖<br>—CH₂COBu(t) | —CMe₃ | –193 (Sublimed) |
| 1-141 | 5'-CH₃ | H | —CMe₃ | 165–170 |
| 1-142 | 5'-CH₃ | H | —CMe₃ | 250–252 |
| 1-143 | 5'-CH₃ | H | —CMe₃ | 222–224 |
| 1-144 | 5'-OCH₂CH=CH₂ | H | —CMe₃ | 162–165 |
| 1-145 | 5'-OCH₂C≡CH | H | —CMe₃ | Amorphous |
| 1-146 | 5'-OCH₂CH=CH₂ | H | —CMe₃ | 129–131 |
| 1-147 | 5'-OCH₂C≡CH | H | —CMe₃ | Amorphous |
| 1-148 | 5'-CH₃ | —COCH₃ | —CMe₃ | Amorphous |

TABLE 12-continued

| | | | | |
|---|---|---|---|---|
| 1-149 | 3'-OCH$_2$CH$_2$OEt | H | —CMe$_3$ | 147–150 |
| 1-150 | 3'-OCH$_2$CH$_2$Br | H | —CMe$_3$ | 136–140 |
| 1-151 | 5'-CH$_3$ | —CH$_2$—CH=CH$_2$ | —CMe$_3$ | Amorphous |
| 1-152 | 5'-CH$_3$ | —CH$_2$CH$_2$OEt | —CMe$_3$ | Amorphous |

TABLE 13

| No. | A | B | R$^1$ | R$^2$ | R$^3$ | R$^4$ | R$^5$ | R$^6$ | R$^7$ | R$^8$ | R$^9$ |
|---|---|---|---|---|---|---|---|---|---|---|---|
| 1-153 | CH$_2$ | O | H | H | H | H | CH$_3$ | H | H | H | H |
| 1-154 | CH$_2$ | O | H | H | H | H | CH$_3$ | H | H | H | 3'-CH$_3$ |
| 1-155 | CH$_2$ | O | H | H | H | H | CH$_3$ | H | H | H | 3'-CH$_3$ |
| 1-156 | CH$_2$ | O | H | H | H | H | CH$_3$ | H | H | H | 3'-CH$_3$ |
| 1-157 | CH$_2$ | O | H | H | H | H | CH$_3$ | H | H | H | 3'-CH$_3$ |
| 1-158 | CH$_2$ | O | H | H | H | H | CH$_3$ | H | H | H | 3'-CH$_3$ |
| 1-159 | O | O | H | H | H | H | CH$_3$ | CHO | H | H | 3'-CH$_3$ |
| 1-160 | O | NH | H | H | H | H | CH$_3$ | H | H | H | 3'-CH$_3$ |
| 1-161 | O | O | H | H | H | H | —OCH$_2$OEt | H | H | H | 3'-CH$_3$ |
| 1-162 | O | O | H | H | H | H | OH | H | H | H | 3'-CH$_3$ |
| 1-163 | O | O | H | H | H | H | CH$_3$ | H | I | H | 3'-CH$_3$ |
| 1-164 | CH$_2$ | O | H | H | H | H | CH$_3$ | H | H | H | 3'-CH$_3$ |

| No. | R$^{10}$ | R$^{11}$ | R$^{12}$ | Melting Point (°C.) |
|---|---|---|---|---|
| 1-153 | 3'-OCH$_2$CH$_2$OEt | H | —CMe$_3$ | 146–148 |
| 1-154 | 5'-CH$_3$ | CH$_3$ | —CMe$_3$ | Amorphous |
| 1-155 | 5'-CH$_3$ | —CH$_2$CO—Bu(t) (O) | —CMe$_3$ | 205–207 |
| 1-156 | 5'-CH$_3$ | —CO$_2$CH$_2$CH(CH$_3$)$_2$ | —CMe$_3$ | Amorphous |
| 1-157 | 5'-CH$_3$ | —CH$_2$CH$_2$CH$_2$Br | —CMe$_3$ | Amorphous |
| 1-158 | 5'-CH$_3$ | CN | —CMe$_3$ | Amorphous |
| 1-159 | 5'-CH$_3$ | H | —CMe$_3$ | 221–223 |
| 1-160 | 5'-CH$_3$ | H | —CMe$_3$ | |
| 1-161 | 5'-CH$_3$ | H | —CMe$_3$ | 121.5–122.5 |
| 1-162 | 5'-CH$_3$ | H | —CMe$_3$ | 182–184 |
| 1-163 | 5'-CH$_3$ | H | —CMe$_3$ | |
| 1-164 | 5'-CH$_3$ | —CH$_2$OC$_2$H$_5$ | —CMe$_3$ | Amorphous |

TABLE 14

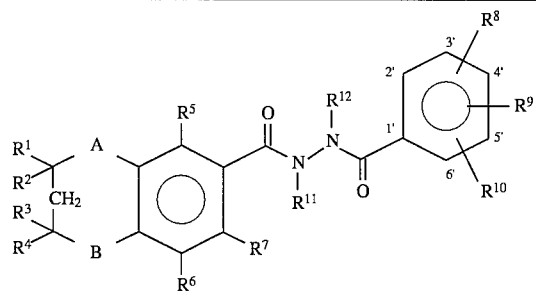

| No. | A | B | R$^1$ | R$^2$ | R$^3$ | R$^4$ | R$^5$ | R$^6$ | R$^7$ | R$^8$ | R$^9$ | R$^{10}$ | R$^{11}$ | R$^{12}$ | Melting Point (°C.) |
|---|---|---|---|---|---|---|---|---|---|---|---|---|---|---|---|
| 2-1 | O | O | H | H | H | H | Me | H | H | H | 3'-Me | 5'-Me | H | —CMe$_3$ | 113–118 |

TABLE 14-continued

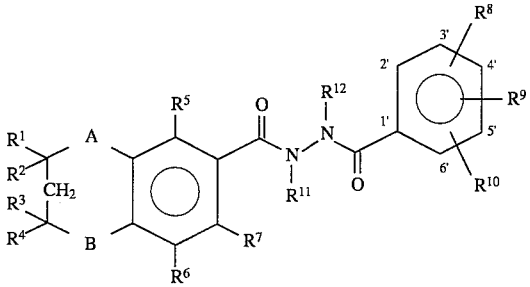

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 2-2 | O | O | H | H | H | H | Me | H | H | H | 3'-Me | 5'-Me | H | —CHMe₂<br>\|<br>CMe₃ | 164–165 |

TABLE 15

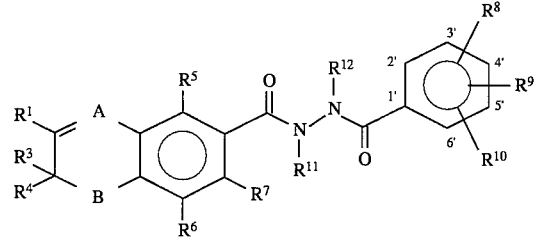

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 3-1 | =CH— | O | H | H | H | H | Me | H | H | H | 3'-Me | 5'-Me | H | CMe₃ | 183–188 |

TABLE 16

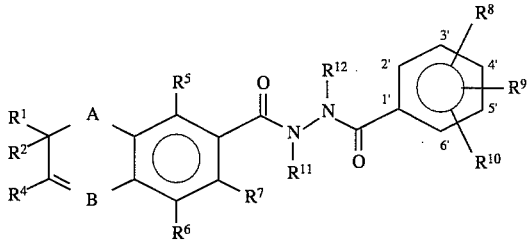

| No. | A | B | R¹ | R² | R³ | R⁴ | R⁵ | R⁶ | R⁷ | R⁸ | R⁹ | R¹⁰ | R¹¹ | R¹² | Melting Point (°C.) |
|---|---|---|---|---|---|---|---|---|---|---|---|---|---|---|---|
| 4-1 | O | =CH— | H | H | H | H | Me | H | H | H | 3'-Me | 5'-Me | H | CMe₃ | 108–110 |
| 4-2 | O | =CH— | Me | Me | H | H | Me | H | H | H | 3'-Me | 5'-Me | H | CMe₃ | 138–139 |
| 4-3 | O | =CMe— | H | H | H | H | Me | H | H | H | 3'-Me | 5'-Me | H | CMe₃ | |

Next, the pesticidal composition is explained specifically by referring to the formulation examples.

Formulation Example 1: Emulsifiable Concentrate

To 20 parts of the compound of Compound No. 1-1 was added 65 parts of a mixed solution of xylene and methylnaphthalene, and then 15 parts of a mixture of an alkylphenol-ethylene oxide condensate and calcium alkylbenzenesulfonate (8:2) was mixed thereto to obtain an emulsifiable concentrate. This formulation is used as a spray solution by diluting it with water.

Formulation Example 2: Wettable Powder

To 20 parts of the compound of Compound No. 1-1, were added 35 parts of kaolin, 30 parts of clay, 7.5 parts of diatomaceous earth, and then 7.5 parts of a mixture of sodium laurate and sodium dinaphthylmethanesulfonate (1:1) was mixed thereto. The mixture was finely pulverized to obtain a wettable powder. This formulation is used as a spreading solution by diluting with water.

Formulation Example 3: Dust

To 1 part of the compound of Compound No. 1-8, was added 97 parts of a mixture of talc and calcium carbonate (1:1) and the mixture was pulverized and sufficiently and uniformly dispersed. Further, 2 parts of anhydrous silicic acid was added, and the mixture was well mixed and pulverized to obtain powder. This powder is used by spray as it is.

Formulation Example 4: Granules

To 2 parts of the compound of Compound No. 1-8, were mixed 48 parts of bentonite fine powder, 48 parts of talc and 2 parts of sodium lignin sulfonate, and then water was added thereto and the mixture was kneaded until it became uniform. Next, the mixture was granulated through an injection molding machine, and passing through a grain uniforming machine and a dryer sieve to prepare a granule having a grain size of 0.6 to 1 mm. This formulation is used by topdressing directly to paddy field surface and soil surface.

Formulation Example 5: Oil

To 0.1 part of the compound of Compound No. 1-1, was added 0.5 part of piperonyl butoxide, and kerosine was added thereto so that the total weight became 100 parts to obtain an oil. This preparation is used as it is.

Formulation Example 6: Water based Flowables 5 parts of the compound of compound No. 1-8 were mixed with 5 parts of Newkalgen (dispersing agent, Takemoto Oil & Fat Co., Ltd.), 0.2 parts of Antifoam 422 (anti-foaming agent, Rhone-Poulenc) and 74.6 parts of distilled water. Then the mixture was milled for 45 minutes at 1,000 rpm. After milling the mixture, 8 parts of propylene glycol, 2 parts of xanthan gum and 7 parts of 1% Proxcel GXL solution were added and mixed.

This formulation (5% water based flowables) is used as a spray solution by diluting it with water.

Next, the pesticidal effects of the hydrazine derivative represented by the formula (I) of the present invention will be specifically described by referring to the following Test Examples.

As the comparative compounds, the following compounds were used.

A: [chemical structure]

(No. 200 of Japanese Patent Application Laid-Open (KOKAI) No. 62-167747 (1987))

B: [chemical structure]

(No. 10 of Japanese Patent Application Laid-Open (KOKAI) No. 3-141245 (1991))

C: [chemical structure]

(No. 9 of Japanese Patent Application Laid-Open (KOKAI) No. 3-141245 (1991))

Test Example 1

Effect to *Plutella xylostella* (foliar dipping method)

According to Formulation Examples 1 and 2, 20% wettable powder or 5% emulsifiable concentrate of the hydrazine derivative according to the present invention was prepared to obtain a test formulation. As a control formulation, prothiophos 50% emulsifiable concentrate and cypermeslin 6% emulsifiable concentrate were used. Test method:

A cabbage leaf of a medium size cut from cabbage grown to decafoliate stage was dipped for 20 seconds in a treatment solution prepared by diluting each of the formulations with water to an effective ingredient concentration of 12.5 ppm. After air-dried, the thus treated leaf was placed in a plastic container having a diameter of 9 cm, and ten *Plutella xylostella* larvae (third instar) were transferred thereon. With covering by a lid having five or six pin holes, the container was left in a temperature-controlled chamber at 25° C. After 4 days from the treatment, the number of live and dead insects were counted to calculate the mortality. The results shown in Table 17 are averages of two replications. *Plutella xylostella* of susceptible strain (collected in Ageo) and of resistant strain (collected in Kagoshima) to organophosphorus pesticides, carbamate pesticides, pyrethroids, etc. were used.

TABLE 17

| Test compound | Mortality (%) Susceptible strain (in Ageo) | Mortality (%) Resistant strain (in Kagoshima) |
| --- | --- | --- |
| 1 - 2 | 100 | 100 |
| 1 - 5 | 100 | 100 |
| 1 - 24 | 100 | 100 |
| 1 - 25 | 100 | 100 |
| 1 - 88 | 100 | 100 |
| 1 - 91 | 80 | 70 |
| 1 - 137 | 100 | 100 |
| 1 - 139 | 100 | 100 |
| 1 - 144 | 100 | 100 |
| A | 80 | 70 |
| B | 50 | 40 |
| C | 40 | 40 |
| Prothiophos 200 ppm | 100 | 0 |
| Agroslin 60 ppm | 100 | 0 |

Test Example 2

Effect to *Spodoptera litura*

According to Formulation Examples 1 and 2, 20% wettable powder or 5% emulsifiable concentrate of the hydrazine derivative according to the present invention was prepared and tested. Test method:

A cabbage leaf of a medium size cut from cabbage grown to decafoliate stage was dipped for 20 seconds in a treatment solution prepared by diluting each of the formulations with water to an effective ingredient concentration of 3 ppm. After air-dried, the thus treated two leaves were placed in a plastic container having a diameter of 9 cm, and five *Spodoptera litura* larvae (third instar) were transferred thereon. With covering by a lid having five or six pin holes, he container was left in a temperature-controlled chamber at 25° C. After 4 days from the treatment, the number of live and dead insects were counted to calculate the mortality. The results shown in Table 18 are averages of two replications.

TABLE 18

| Test compound | Mortality (%) |
| --- | --- |
| 1 - 1 | 100 |
| 1 - 2 | 100 |
| 1 - 3 | 70 |
| 1 - 5 | 100 |
| 1 - 8 | 90 |
| 1 - 13 | 100 |
| 1 - 15 | 100 |
| 1 - 19 | 100 |
| 1 - 21 | 100 |
| 1 - 23 | 100 |
| 1 - 24 | 100 |
| 1 - 25 | 90 |
| 1 - 29 | 90 |
| 1 - 34 | 100 |
| 1 - 40 | 100 |
| 1 - 42 | 100 |
| 1 - 46 | 100 |
| 1 - 88 | 100 |
| 1 - 91 | 100 |
| 1 - 92 | 100 |
| 1 - 93 | 100 |
| 1 - 94 | 80 |
| 1 - 96 | 100 |
| 1 - 100 | 80 |
| 1 - 103 | 90 |
| 1 - 112 | 70 |
| 1 - 118 | 100 |
| 1 - 119 | 100 |
| 1 - 123 | 80 |
| 1 - 136 | 100 |
| 1 - 137 | 100 |
| 1 - 139 | 100 |
| 1 - 158 | 100 |
| A | 70 |
| B | 30 |
| C | 20 |

Test Example 3

Effect to *Cnaphalocrocis medinalis*

According to Formulation Examples 1 and 2, 20% wettable powder or 5% emulsifiable concentrate of the hydrazine derivative according to the present invention was prepared and tested. Test method:

In a treatment solution prepared by diluting each of the formulations with water to an effective ingredient concentration of 1 ppm, ten rice plants of in the trifoliate were dipped for 20 seconds. After air-dried, the rice plants were wound with a urethane and fixed in a glass cylinder (inner diameter 44 mm, height 140 mm), and five *Cnaphalocrocis medinalis* larvae (third instar) were transferred into the cylinder. After covered with a paper used for wrapping powdered medicine, the cylinder was kept still at 25° C. in a temperature-controlled chamber of 16-hour diurnal. After 5 days after the treatment, the number of live and dead insects were counted to calculate the mortality. The test was carried out in two replications and susceptible strain of *Cnaphalocrocis medinalis* was tested. The results are shown in Table 19.

TABLE 19

| Test compound | Mortality (%) |
| --- | --- |
| 1 - 2 | 90 |
| 1 - 12 | 100 |
| 1 - 15 | 100 |
| 1 - 39 | 100 |
| 1 - 40 | 100 |
| 1 - 46 | 100 |
| 1 - 48 | 100 |
| 1 - 50 | 100 |
| 1 - 88 | 100 |
| 1 - 139 | 100 |
| 1 - 158 | 100 |
| A | 80 |
| B | 0 |
| C | 0 |

Test Example 4

Effect to *Adoxophyes orana*

According to Formulation Examples 1 and 2, 20% wettable powder or 5% emulsifiable concentrate of the hydrazine derivative according to the present invention was prepared and tested. Test method:

Seven green tea leaves with a length of about 5 cm were dipped for 20 seconds in a treatment solution prepared by diluting each of the formulations with water to an effective ingredient concentration of 3 ppm. After air-dried, the thus treated leaves were placed in a plastic container (inner diameter 70 mm, height 40 mm), and five *Adoxophyes orana* larvae (third instar) were transferred thereinto. The container was covered with a lid having 5 to 6 pin holes and allowed to stand at 25° C in a temperature-controlled chamber of 16-hour diurnal. After 5 days from the treatment, the number of live and dead insects were counted to calculate the mortality. The test was carried out in two replications and susceptible strain of *Adoxophyes orana* was tested. The results are shown in Table 20.

TABLE 20

| Test compound | Mortality (%) |
|---|---|
| 1 - 2 | 100 |
| 1 - 8 | 90 |
| 1 - 13 | 100 |
| 1 - 15 | 100 |
| 1 - 21 | 50 |
| 1 - 23 | 100 |
| 1 - 24 | 100 |
| 1 - 40 | 100 |
| 1 - 88 | 60 |
| 1 - 137 | 100 |
| 1 - 139 | 60 |
| A | 40 |
| B | 30 |
| C | 20 |

Test Example 5

Effect to *Plutella xylostella* (root dipping method)

According to Formulation Examples 1 and 2, 20% wettable powder or 5% emulsifiable concentrate of the hydrazine derivative according to the present invention was prepared and tested.

Test method:

White radish sprout of which cotyledon was opened were pulled out from soil and after washing with water, the root thereof was dipped for 2 days in a treatment solution prepared by diluting each of the formulations with water to an effective ingredient concentration of 20 ppm. The white radish sprout thus treated was placed in a glass cylinder having a diameter of 5 cm and a height of 15 cm, and *Plutella xylostella* larvae (third instar) were transferred thereinto. After the glass cylinder was covered with a paper used for wrapping powdered medicine, the cylinder was allowed to stand in a temperature-controlled chamber at 25° C. After 3 days from the treatment, the number of live and dead insects were counted to calculate the mortality. The test was carried out in two replications each containing five larvae and an average value of the mortalities were shown in Table 21. The susceptible strain of *Plutella xylostella* (collected in Ageo) were tested.

TABLE 21

| Test compound | Mortality (%) |
|---|---|
| 1 - 5 | 100 |
| 1 - 6 | 90 |
| 1 - 7 | 100 |
| 1 - 9 | 90 |
| 1 - 11 | 60 |
| 1 - 19 | 100 |
| 1 - 23 | 100 |
| 1 - 24 | 80 |
| 1 - 25 | 100 |
| 1 - 27 | 80 |
| 1 - 43 | 80 |
| 1 - 44 | 70 |
| 1 - 51 | 90 |
| 1 - 57 | 100 |
| 1 - 59 | 100 |
| 1 - 96 | 100 |

TABLE 21-continued

| Test compound | Mortality (%) |
|---|---|
| 1 - 117 | 100 |
| 1 - 121 | 100 |
| 1 - 144 | 100 |
| 1 - 145 | 100 |
| 2 - 2 | 100 |
| A | 0 |
| B | 0 |
| C | 0 |

What is claimed is:

1. A hydrazine derivative represented by the following formula (I):

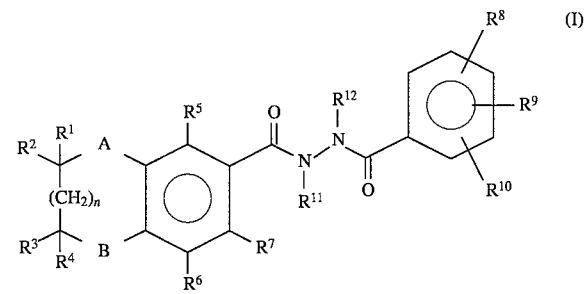

wherein

A represents —O—;

B represents —O—;

$R^1$, $R^2$, $R^3$ and $R^4$ each independently represent a hydrogen atom, a methyl group, a $(C_1-C_4)$alkoxy$(C_1-C_4)$alkyl group or a benzyloxy$(C_1-C_4)$alkyl group;

$R^5$ represents a $(C_1-C_4)$alkyl group, a $(C_1-C_4)$haloalkyl group, a halogen atom, a nitro group, an amino group, a cyano group, a hydroxy group, a $(C_2-C_4)$alkenyl group, a $(C_1-C_4)$alkoxy group, a $(C_1-C_4)$alkoxy$(C_1-C_4)$alkoxy group or a $(C_1-C_4)$alkylthio$(C_1-C_4)$alkyl group;

$R^6$ represents a hydrogen atom, a $(C_1-C_4)$alkyl group, a halogen atom, a $(C_1-C_4)$haloalkyl group or a formyl group;

$R^7$ represents a hydrogen atom, a halogen atom or a nitro group;

$R^8$, $R^9$ and $R^{10}$ each independently represents a hydrogen atom, a $(C_1-C_4)$alkyl group, a $(C_1-C_4)$haloalkyl group, a halogen atom, a nitro group, a $(C_1-C_4)$alkoxy group, a $(C_2-C_4)$alkenyloxy group, a $(C_2-C_4)$alkynyloxy group, a $(C_2-C_4)$alkenyl group, a $(C_2-C_4)$alkynyl group, a $(C_1-C_4)$haloalkoxy group, a $(C_1-C_4)$alkoxy$(C_1-C_4)$alkoxy group, a phenyl$(C_1-C_4)$alkoxy group whose phenyl moiety is optionally substituted with a halogen atom, or a phenoxy$(C_1-C_4)$alkoxy group whose phenyl moiety is optionally substituted with a $(C_1-C_2)$alkyl group, $CF_3$ or halogen atom;

$R^{11}$ represents a hydrogen atom, a $(C_1-C_4)$alkyl group, a $(C_2-C_4)$alkenyl group, a $(C_1-C_4)$haloalkyl group, a $(C_2-C_4)$alkanoyl group, a $(C_1-C_4)$alkoxycarbonyl group, a $(C_1-C_4)$alkoxycarbamoyl group, a $(C_1-C_4)$alkoxy$(C_1-C_4)$alkyl group, a cyano group a $(C_1-C_4)$haloalkylthio group, a $(C_1-C_4)$alkoxycarbonylcarbonyl group, or a $(C_1-C_4)$alkylcarbonyloxymethyl group;

$R^{12}$ represents a branched $(C_4-C_8)$alkyl group; and n represents 0 or 1.

2. A hydrazine derivative according to claim 1, wherein

A represents —O—;

B represents —O—;

$R^1$, $R^2$, $R^3$ and $R^4$ each independently represent a hydrogen atom or a methyl group;

$R^5$ represents a ($C_1$–$C_4$)alkyl group, a ($C_2$–$C_4$)alkenyl group, a ($C_1$–$C_4$)haloalkyl group or a halogen atom;

$R^6$ represents a hydrogen atom, a ($C_1$–$C_4$)alkyl group or a halogen atom;

$R^7$ represents a hydrogen atom or a halogen atom;

$R^8$, $R^9$ and $R^{10}$ each independently represents a hydrogen atom, a ($C_1$–$C_4$)alkyl group, a ($C_1$–$C_4$)haloalkyl group, a halogen atom, a nitro group, a ($C_1$–$C_4$)alkoxy group, a ($C_2$–$C_4$)alkenyloxy group, a ($C_2$–$C_4$)alkynyloxy group, a ($C_2$–$C_4$)alkenyl group, a ($C_1$–$C_4$)haloalkoxy group, a phenyl($C_1$–$C_4$)alkoxy group whose phenyl moiety is optionally substituted with a halogen atom, or a phenoxy($C_1$–$C_4$)alkoxy group whose phenyl moiety is optionally substituted with a ($C_1$–$C_2$)alkyl group, $CF_3$ or halogen atom;

$R^{11}$ represents a hydrogen atom, a cyano group, a ($C_1$–$C_4$)haloalkylthio group, a ($C_1$–$C_4$)alkoxycarbonylcarbonyl group or a ($C_1$–$C_4$)alkylcarbonyloxymethyl group;

$R^{12}$ represents a branched ($C_4$–$C_8$)alkyl group; and n represents 0 or 1.

3. A hydrazine derivative according to claim 1, wherein

A represents —O—;

B represents —O—;

$R^1$, $R^3$ and $R^4$ each represents a hydrogen atom;

$R^2$ represents a hydrogen atom or a methyl group;

$R^5$ represents a ($C_1$–$C_2$)alkyl group or a halogen atom;

$R^6$ represents a hydrogen atom;

$R^7$ represents a hydrogen atom or a halogen atom;

$R^8$, $R^9$ and $R^{10}$ each independently represents a hydrogen atom, a ($C_1$–$C_2$)alkyl group, a ($C_1$–$C_3$)haloalkyl group, a halogen atom, a nitro group or a ($C_1$–$C_2$)alkoxy group, a ($C_1$–$C_3$)haloalkoxy group, a ($C_1$–$C_3$)alkenyloxy group or a ($C_1$–$C_3$)alkynyloxy group;

$R^{11}$ represents a hydrogen atom, a cyano group or a trichloromethylthio group $R^{12}$ represents a branched ($C_4$–$C_6$)alkyl group; and n represents 0.

4. A hydrazine derivative according to claim 1, wherein

A represents —O—;

B represents —O—;

$R^1$, $R^2$, $R^3$ and $R^4$ each represents a hydrogen atom;

$R^5$ represents a ($C_1$–$C_2$)alkyl group or a chlorine atom;

$R^6$ represents a hydrogen atom;

$R^7$ represents a hydrogen atom or a fluorine atom;

$R^8$, $R^9$ and $R^{10}$ each independently represents a hydrogen atom, a methyl group, an ethyl group, an allyloxy group, a chlorine atom, a fluorine atom, a nitro group or a methoxy group;

$R^{11}$ represents a hydrogen atom, a cyano group or a trichloromethylthio group;

$R^{12}$ represents a branched ($C_4$–$C_6$)alkyl group; and n represents 0.

5. A hydrazine derivative according to claim 1, wherein

B represents —O—;

$R^1$, $R^2$, $R^3$ and $R^4$ each represents a hydrogen atom;

$R^5$ represents a ($C_1$–$C_2$)alkyl group;

$R^6$ represents a hydrogen atom;

$R^7$ represents a hydrogen atom;

$R^8$, $R^9$ and $R^{10}$, together with the phenyl group to which they are attached, represent a 3,5-dimethylphenyl group, a 3,5-dichlorophenyl group or a 3,5-dimethyl-4-fluorophenyl group;

$R^{11}$ represents a hydrogen atom, a cyano group or a trichloromethylthio group; and $R^{12}$ represents a t-butyl group, a 2,2-dimethylpropyl group or a 1,2,2-trimethylpropyl group.

6. A hydrazine derivative according to claim 1, which is selected from the group consisting of:

N-(5-methyl-1,4-benzodioxan-6-carbonyl)-N'-(2,2-dimethylpropyl)-N'-(3,5-dimethylbenzoyl)hydrazine, N-cyano-N-(5-methyl-1,4-benzodioxan-6-carbonyl)-N'-t-butyl-N'-(3,5-dimethylbenzoyl)hydrazine, N-(5-methyl-1,4-benzodioxan-6-carbonyl)-N-trichloromethylthio-N'-t-butyl-N'-(3,5-dimethylbenzoyl)hydrazine, N-(5-methyl-1,4-benzodioxan-6-carbonyl)-N'-t-butyl-N'-(3,5-dichlorobenzoyl)hydrazine, N-(5-methyl-1,4-benzodioxan-6-carbonyl)-N'-t-butyl-N'-(3-difluoromethyl-5-methylbenzoyl)hydrazine, N-(5-methyl-1,4-benzodioxan-6-carbonyl)-N'-(1,2,2-trimethylpropyl)-N'-(3,5-dimethylbenzoyl)hydrazine, and N-(5-methyl-1,4-benzodioxan-6-carbonyl)-N'-t-butyl-N'-(3,5-dimethylbenzoyl)hydrazine.

7. A pesticidal composition which comprises a pesticidally effective amount of the hydrazine derivative as defined in claim 1 as an effective ingredient and a pesticidally acceptable adjuvant.

8. A pesticidal composition which comprises a pesticidally effective amount of the hydrazine derivative as defined in claim 2 as an effective ingredient and a pesticidally acceptable adjuvant.

9. A pesticidal composition which comprises a pesticidally effective amount of the hydrazine derivative as defined in claim 3 as an effective ingredient and a pesticidally acceptable adjuvant.

10. A pesticidal composition which comprises a pesticidally effective amount of the hydrazine derivative as defined in claim 4 as an effective ingredient and a pesticidally acceptable adjuvant.

11. A pesticidal composition which comprises a pesticidally effective amount of the hydrazine derivative as defined in claim 5 as an effective ingredient and a pesticidally acceptable adjuvant.

12. A pesticidal composition which comprises a pesticidally effective amount of the hydrazine derivative as defined in claim 6 as an effective ingredient and a pesticidally acceptable adjuvant.

13. A method for controlling a harmful pest which comprises applying the hydrazine derivative as defined in claim 1 to the harmful pest.

14. A method for controlling a harmful pest which comprises applying the hydrazine derivative as defined in claim 2 to the harmful pest.

15. A method for controlling a harmful pest which comprises applying the hydrazine derivative as defined in claim 3 to the harmful pest.

16. A method for controlling a harmful pest which comprises applying the hydrazine derivative as defined in claim 4 to the harmful pest.

17. A method for controlling a harmful pest which comprises applying the hydrazine derivative as defined in claim 5 to the harmful pest.

18. A method for controlling a harmful pest which comprises applying the hydrazine derivative as defined in claim 6 to the harmful pest.

* * * * *